US006002068A

United States Patent [19]
Privalle et al.

[11] Patent Number: 6,002,068
[45] Date of Patent: Dec. 14, 1999

[54] METHODS FOR CONFERRING INSECT RESISTANCE TO A MONOCOT USING A PERIOXIDASE CODING SEQUENCE

[75] Inventors: Laura Privalle; Juan Estruch, both of Durham; Martha Wright, Cary; Martha Beale Hill, Hillsborough, all of N.C.; Patrick Francis Dowd, Peoria, Ill.; Lawrence Mark Lagrimini, Hilliard, Ohio

[73] Assignees: Novartis Finance Corporation, New York, N.Y.; The Ohio State University, Columbus, Ohio; The United States of America as represented by the Secretary of Agriculture, Washington, D.C.

[21] Appl. No.: 08/770,097

[22] Filed: Dec. 19, 1996

[51] Int. Cl.$^6$ .............................. C12N 5/04; C12N 15/84; C12N 15/82; A01H 5/00
[52] U.S. Cl. ........................ 800/279; 435/69.1; 435/468; 800/293; 800/292; 800/294
[58] Field of Search .................................. 435/418, 69.1, 435/468, 410, 412, 419, 320.1; 800/205, DIG. 52, DIG. 56, DIG. 57, 278, 279, 290, 292, 293, 294, 295, 300.1, 298, 320.1

[56] References Cited

FOREIGN PATENT DOCUMENTS

| | | |
|---|---|---|
| WO 93/06212 | 4/1993 | WIPO . |
| WO 94/13822 | 6/1994 | WIPO . |
| WO 94/21795 | 9/1994 | WIPO . |
| WO 95/08914 | 4/1995 | WIPO . |
| WO 96/10083 | 4/1996 | WIPO . |

OTHER PUBLICATIONS

Carvalho et al. The EMBO Journal. 1992. vol. 11: 5995–5602.
Wan and Lemaux. Plant Physiol. 1994. vol. 104: 37–48.
Matzke and Matzke. Plant Physiol. 1995. vol. 679–685.
Fromm et al. Bio/Technology. 1990. vol. 8: 833–839.
Lagrimini . Plant Physiol. 1991. vol. 96: 577–583.
Koziel et al. Bio/Technology. 1993. vol. 11: 194–200.
Bergvinson, D.J. et al., "Leaf Profile of Maize Resistance Factors to European Corn Borer, *Ostrinia nubilalis*," *J. Chem. Ecol.* 21(3):343–354 (Mar. 1995).
Bergvinson, D.J. et al., "Effect of Light on Changes in Maize Resistance Against the European Corn Borer, *Ostrinia nubilalis* (Húbner)," *Can. Entomol.* 127:111–122 (Jan./Feb. 1995).
Bergvinson, D.J. et al., "Putative Role of Photodimerized Phenolic Acids in Maize Resistance to *Ostrinia nubilalis*," *Environ. Entomol.* 23(6):1516–1523 (1994).
Bergvinson, D.J. et al., "Determining Leaf Toughness and Its Role in Maize Resistance to the European Corn Borer (Lepidoptera: Pyralidae)," *J. Econ. Entomol.* 87(6):1743–1748 (1994).

Bronner, R. et al., "Enhanced peroxidase activity associated with the hypersensitive response of *Solanum dulcamara* to the gall mite *Aceria cladophthirus* (Acari: Eriophyoidea)," *Can. J. Bot.* 69:2192–2196 (1991).
Buendgen, M.R. et al., "European Corn Borer Resistance and Cell Wall Composition of Three Maize Populations," *Crop Sci.* 30:505–510 (1990).
Byrne, P.F. et al., "Maize Silk–Browning, Maysin Content, and Antibiosis to the Corn Earworm, *Helicoverpa zea* (Boddie)," *Maydica* 41:13–18 (1996).
Casas, A.M. et al., "Transgenic sorghum plants via microprojectile bombardment," *Proc. Natl. Acad. Sci. USA* 90:11212–11216 (1993).
Christou, P. et al., "Production of Transgenic Rice (*Oryza sativa* L.) Plants from Agronomically Imortant Indica and Japonica Varieties via Electric Discharge Particle Acceleration of Exogenous DNA into Immature Zygotic Embryos," *Bio/Technol.* 9:957–962 (1991).
Coors, J.G., "Resistance to the European corn borer, *Ostrinia nubilalis* (Hubner), in maize, *Zea mays* L. as affected by soil silica, plant silica, structural carbohydrates, and lignin," in: *Genetic Aspects of Plant Mineral Nutrition*, H.W. Gableman and B.C. Loughman, eds., Martinus Nijhoff Publishers, Dordrecht, pp. 445–456 (1987).
Datta, S.K. et al., "Genetically Engineered Fertile Indica–Rice Recovered from Protoplasts," *Bio/Technol* 8:736–740 (1990).
Dowd, P.F., "Enhanced Maize (*Zea mays* L.) Pericarp Browning: Associations with Insect Resistance and Involvment of Oxidizing Enzymes," *J. Chem. Ecol.* 20(11):2777–2803 (1994).
Dowd, P.F., "Sap beetles and mycotoxins in maize," *Food Add. and Contam.* 12(3):497–508 (1995).
Dowd, P.F. and R.A. Norton, "Browning–Associated Mechanisms of Resistance to Insects in Corn Callus Tissue," *J. Chem. Ecol.* 21(5):583–600 (1995).
Dowd, P.F., "Corn Kernel Aryl Alcohol Oxidases as Cross–Resistance Mechanisms for Fungi and Insects," *Abstracts of Papers Presented at the 203rd ACS National Meeting*, Abstract No. 107 (1992).
Felton, G.W. and C.G. Summers, "Antioxidant Systems in Insects," *Arch. Insect Biochem. Physiol.* 29:187–197 (1995).

(List continued on next page.)

*Primary Examiner*—Elizabeth F. McElwain
*Assistant Examiner*—Ousama M-Fait Zoghmout
*Attorney, Agent, or Firm*—J. Timothy Meigs; Gary M. Pace

[57] ABSTRACT

The present invention relates, in general, to methods and compositions for controlling insects in monocotyledonous plants (monocots), particularly maize. More precisely, the present invention relates to (1) a method for controlling insects comprising feeding or contacting an insect with an insecticidal amount of transgenic monocotyledonous plant cells comprising a recombinant DNA sequence comprising a coding sequence encoding peroxidase and (2) a fertile transgenic monocot plant comprising a recombinant DNA sequence comprising a coding sequence encoding peroxidase.

21 Claims, 2 Drawing Sheets

OTHER PUBLICATIONS

Felton, G.W. et al., "Avoidance of Antinutritive Plant Defense: Role of Midgut pH in Colorado Potato Beetle," *J. Chem. Ecol. 18*(4): 571–583 (1992).

Felton, G.W. and S.S. Duffy, "Protective Action of Midgut Catalase in Lepidopteran Larvae Against Oxidative Plant Defenses," *J. Chem. Ecol. 17*(9):1715–1732 (1991).

Grand, C. et al., "Comparison of lignins and of enzymes involved in lignification in normal and brown midrib (bm$_3$) mutant corn seedlings," *Physiol Veg. 23*(6):905–911 (1985).

Hayashimoto, A. et al., "A Polyethylene Glycol–Mediated Protoplast Transformation System for Production of Fertile Transgenic Rice Plants," *Plant Physiol. 93*:857–863 (1990).

Jähne, A. et al., "Regeneration of transgenic, microspore–derived, fertile barley," *Theor. Appl. Genet. 89*:525–533 (1994).

Koziel, M.G. et al., "The Insecticidal Crystal Proteins of *Bacillus thuringiensis*: Past, Present and Future Uses," *Biotech. Genet. Engineer. Rev. 11*:171–227 (1993).

Lagrimini, L.M. et al., "Molecular cloning of complimentary DNA encoding the lignin–forming peroxidase from tobacco: Molecular analysis and tissue–specific expression," *Proc. Natl. Acad. Sci. USA 84*:7542–7546 (1987).

Lagrimini, L.M. and S. Rothstein, "Tissue Specificity of Tobacco Peroxidase Isozymes and Their Induction by Wounding and Tobacco Mosaic Virus Infection," *Plant Physiol. 84*:438–442 (1987).

Lagrimini, L.M. et al., "Peroxidase–Induced Wilting in Transgenic Tobacco Plants," *Plant Cell 2*:7–18 (1990).

Lagrimini, L.M., "Wound–Induced Deposition of Polyphenols in Transgenic Plants Overexpressing Peroxidase," *Plant Physiol. 96*:577–583 (1991).

Lagrimini, L.M. et al., "Expression of a Chimeric Tobacco Peroxidase Gene in Transgenic Tomato Plants," *J. Amer. Soc. Hort. Sci. 117*(6):1012–1016 (1992).

Lagrimini, L.M. et al., "Peroxidase Overproduction in Tomato: Wound–induced Polyphenol Deposition and Disease Resistance," *HortScience 28*(3):218–221 (1993).

Lagrimini, L.M., Poster presentation to the Midwest Plant Biotechnology Consortium, "Advantages of Peroxide-–Based Resistance," (Nov. 1992).

Lagrimini, L.M., Proposal to the Midwest Plant Biotechnology Consortium, "Enhancement of Natural Insect Resistance in Genetically–Modified Maize," (1992).

Miles, P.W. and J.J. Oertli, "The significance of antioxidants in the aphid–plant interaction: the redox hypothesis," *Entomol. Exp. Appl. 67*:275–283 (1993).

Muller, L.D. et al., "Variations in Lignin and Other Structural Components of Brown Midrib Mutants of Maize," *Crop. Sci. 11*:413–415 (1971).

Nehra, N.S. et al., "Self–fertile transgenic wheat plants regenerated from isolated scutellar tissues following microprojectile bombardment with two distinct gene constructs," *Plant J. 5*(2):285–297 (1994).

Nicholson, R.L. et al., "Association of Fusarium Moniliforme with Brown Midrib Maize," *Plant Dis. Rep. 60*(11):908–910 (1976).

Shimamoto, K. et al., "Fertile transgenic rice plants regenerated from transformed protoplasts," *Nature 338*:274–276 (1989).

Somers, D.A. et al., "Fertile, Transgenic Oat Plants," *Bio/Technol 10*:1589–1594 (1992).

Torbert, K.A. et al., "Use of paromomycin as a selective agent for oat transformation," *Plant Cell Rep. 14*:635–640 (1995).

Wan, Y. and P.G. Lemaux, "Generation of Large Numbers of Independently Transformed Fertile Barley Plants," *Plant Physiol 104*:37–48 (1994).

Weeks, J.T. et al., "Rapid Production of Multiple Independent Lines of Fertile Transgenic Wheat (*Triticum aestivum*)," *Plant Physiol. 102*:1077–1084 (1993).

Deng, W. et al., "Plant Lipid Peroxidation Manipulation and Effects on Aphid Resistance," *Plant Physiol. Suppl. 99*:109 (1992).

Dowd, P.F., "Enhanced Maize (*Zea mays* L.) Pericarp Browning: Associations with Insect Resistance and Involvement of Oxidizing Enzymes," *J. Chem. Ecology 20*:2777–2803 (1994).

Dowd, P.F. and R.A. Norton, "Browing–Associated Mechanisms of Resistance to Insects in Corn Callus Tissue," *J. Chem. Ecology 21*:583–600 (Nov. 1995).

Dowd, P.F. adn F.E. Vega, "Enzymatic Oxidation Products of Allelochemicals as a Basis for Resistance Against Insects: Effects on the Corn Leafhopper *Dalbulus maidis*," *Natural Toxins 4*:85–91 (Apr. 1996).

Dowd, P.F. and L.M. Lagrimini, "Examination of Different Tobacco (Nicotiana spp.) Types Under– and Overproducing Tobacco Anionic Peroxidase for their Leaf Resistance to *Helicoverpa zea*," *J. Chem. Ecology 23*:2357–2370 (1997).

Fütterer, J. "Towards Genetically Engineered Fungus Resistance for Rice," *Experentia 52*:A19 (Feb. 1996).

Sullivan, J. and L.M. Lagrimini, "Transformation of *Liquidambar styraciflua* using *Agrobacterium tumefaciens*," *Plant Cell Reports 12*:303–306 (1993).

International Search Report for International Application No. PCT/EP97/07089.

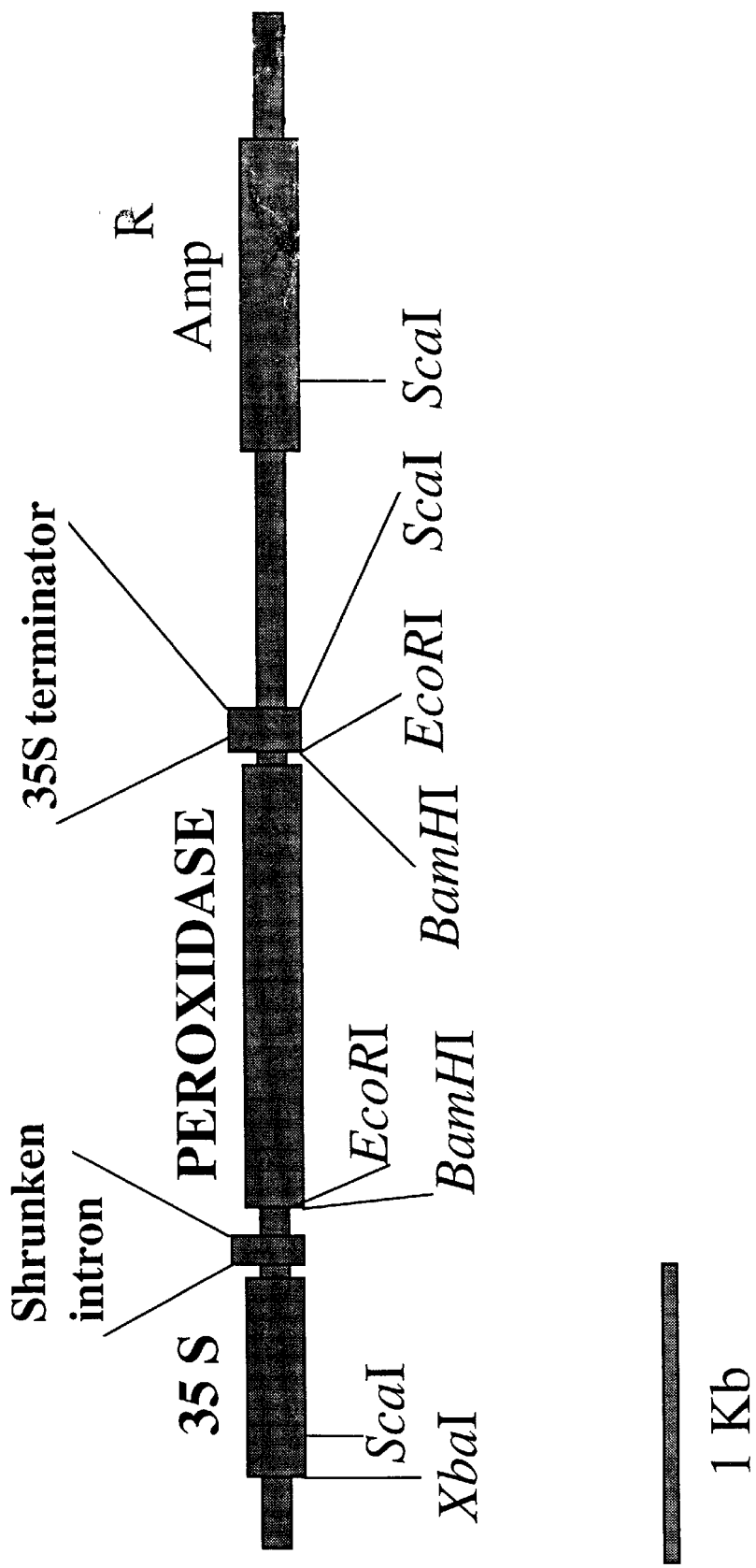
Fig. 1. Plasmid pJS20293.

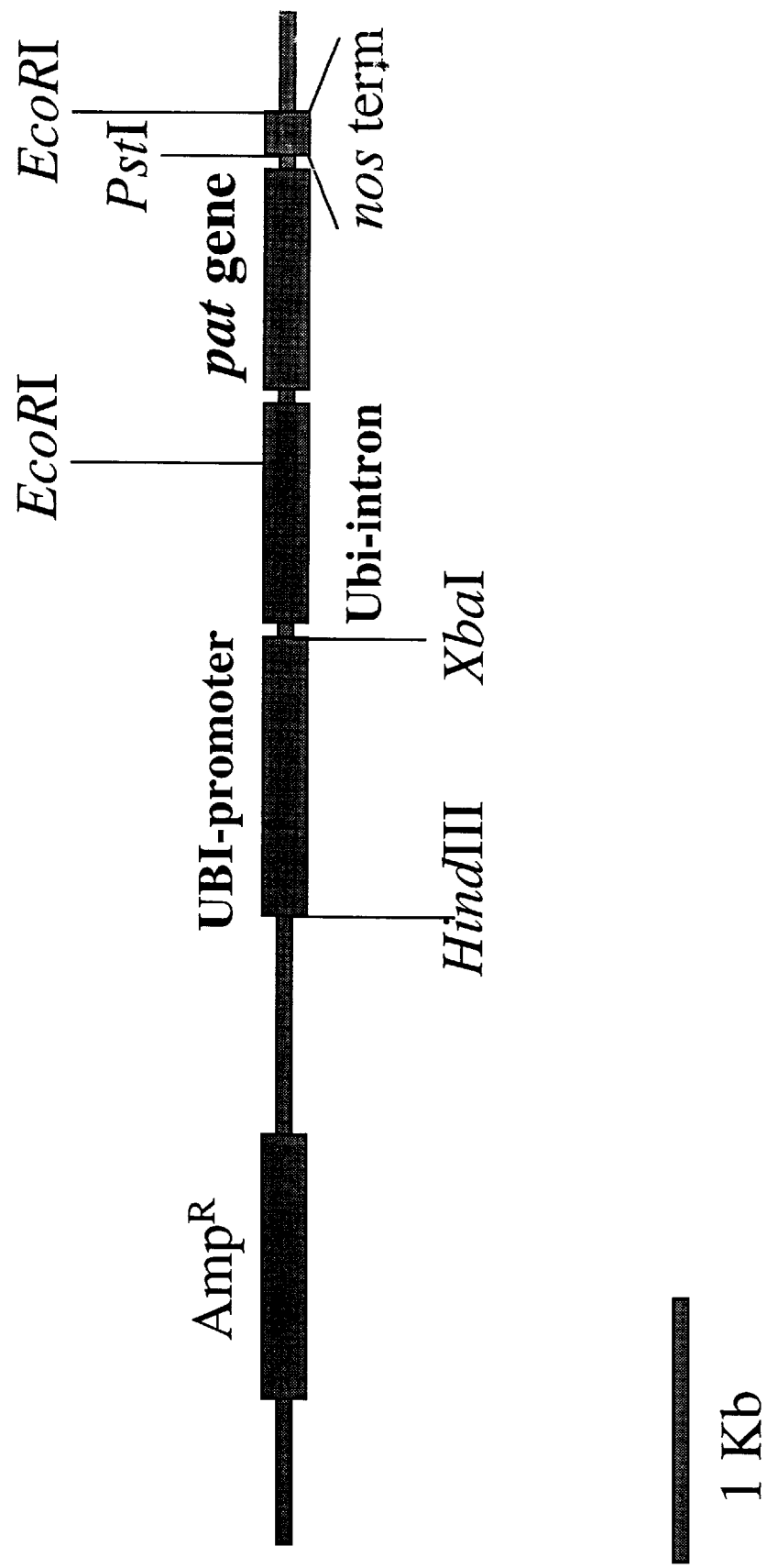
Fig. 2. Plasmid pUBIAc.

METHODS FOR CONFERRING INSECT RESISTANCE TO A MONOCOT USING A PERIOXIDASE CODING SEQUENCE

STATEMENT OF GOVERNMENT RIGHTS IN THE INVENTION

Part of the work performed during development of this invention utilized U.S. Government funds. The U.S. Government has certain rights in this invention.

BACKGROUND OF THE INVENTION

1. Field of the Invention

The present invention relates, in general, to methods and compositions for controlling insects in monocotyledonous plants (monocots), particularly maize. More precisely, the present invention relates to (1) a method for controlling insects comprising feeding or contacting an insect with an insecticidal amount of transgenic monocotyledonous plant cells comprising recombinant DNA comprising a coding sequence encoding peroxidase and (2) a fertile transgenic monocot plant comprising recombinant DNA comprising a coding sequence encoding peroxidase.

2. Background Information

Insect pests are a major factor in the loss of the world's commercially important agricultural crops. Broad spectrum chemical pesticides have been used extensively to control or eradicate pests of agricultural importance. Although insecticides have been effective in controlling most harmful insects, there are considerable problems associated with the use of these compounds. Insecticides are expensive and costly to apply. Often repeated applications are necessary for effective control. There is also concern that insects have or will become resistant to many of the chemicals used in controlling them. Insecticides often kill beneficial insects which are pollinators or prey on the herbivorous insects. Additionally, there are environmental hazards associated with the long term use of chemical insecticides.

Programs of pest management are being introduced which lower the use of chemical insecticides. These programs include the improvement of crops by selection, the employment of biological control agents and insect predators, and the incorporation of insect resistant genes through breeding programs and genetic engineering. The most widely utilized genes for genetic engineering are the crystal protein genes from *Bacillus thuringiensis*. See, for example, Rice et al., EP 292,435 (to Ciba-Geigy AG) and Koziel et al., WO 93/07278 (to Ciba-Geigy AG). The majority of the crystal proteins made by Bacillus are toxic to larvae of insects in the orders Lepidoptera, Diptera and Coleoptera. In general, when an insecticidal crystal protein is ingested by a susceptible insect, the crystal is solubilized and acts as a toxic moiety. To avoid the development of insects which are resistant to these toxins, additional toxins are needed which have additive or synergistic affects.

Peroxidases are a subclass of oxido-reductases that use a peroxide such as $H_2O_2$ as an oxygen acceptor. Peroxidases are heme-containing monomeric glycoproteins able to bind divalent cations (mainly $Ca^{2+}$, but also $Mn^{2+}$) (Maranon and Van Huystee, *Phytochemistry* 37: 1217–1225 (1994)). The prosthetic groups for peroxidase have different roles. While the heme group is involved in catalysis, the divalent cations stabilize the heme moiety, and the glycosyl groups may help to stabilize the peroxidase by decreasing its turnover rate (Maranon and Van Huystee, *Phytochemistry* 37: 1217–1225 (1994)).

Peroxidases are often grouped into anionic, cationic, and neutral forms according to their migration on isoelectric focusing gels. Although as enzymes they are considered to have wide substrate specificity, they do appear to have some substrate "preferences" for different isoenzymes (Van Huystee, *Ann. Rev. Plant Phyisiol.*, 205–219 (1987)). There are several types of peroxidases and related enzymes including guaiacol peroxidase, NADH peroxidase, cytochrome-C peroxidase, catalase, glutathione peroxidase, L-ascorbate peroxidase, and manganese peroxidase.

In plants, peroxidases are monomeric proteins which are highly complex enzymes whose activities are closely regulated by the plant. Peroxidases are critical in the biosynthesis of plant cell walls. Peroxidases promote the peroxidative polymerization of the monolignols coniferyl, ρ-coumaryl, and sinapyl alcohol into lignin (Greisbach, In: *The Biochemistry of Plants,* Ed. Conn, Academic, New York pp. 457–480 (1991)). Different plant species have varying ratios of the monolignol species assembled in a semi-random fashion (Hwang et al., *Carbohydrate Polymers* 14:77–88 (1991)). Lignification serves to strengthen and reinforce cell walls. The overall result is a toughening of the plant tissue.

A tobacco anionic peroxidase was utilized to transform *N. tabacum* and *N. sylvestris* (Lagrimini, *Plant Cell* 2:7–18 (1990); Lagrimini, Plant Physiology 96:577–583 (1991)). These transgenic plants constitutively overexpressed a tobacco anionic peroxidase from a 35S promoter. The most striking phenotype of peroxidase overexpression was chronic wilting which begins at approximately the time of flowering. In addition, the plants were retarded in growth, had smaller, compacted cells, and brown rapidly in response to wounding.

The same construct was also utilized to transform tomato plants (Lagrimini et al., *J Am. Soc. Hort. Sci.* 117:1012–1016 (1992); Lagrimini et al., *Hortscience* 28:218–221(1993)). These plants were also found to wilt severely after flowering, and showed excessive browning and reduced fruit size.

Initial studies have shown that some tissues of transgenic tobacco and tomato plants expressing a tobacco anionic peroxidase gene were resistant to some insects (Dowd et al., presentation at the National Meeting of the Entomological Society of America, Indianapolis, December 1993). Tobacco and tomato are closely related dicots belonging to the same family, the Solanaceae.

In contrast, the transgenic monocots of the present invention have vastly different physiology, biochemistry, anatomy, and metabolism when compared to dicots. For example, monocots have different codon usage, use C4 instead of C3 metabolism, have different fatty acid content, imperfect flowers, and the like. Thus, it was unknown whether substrates would exist in monocots that could be used by peroxidase to control insects.

Further, peroxidases are glycoproteins that must undergo specific post-transcriptional modification and incorporation of heme-containing groups to be stable and enzymatically active. Peroxidases are involved in the synthesis of secondary metabolites and lignins whose nature depends on the substrates available in the specific plant. Therefore, the final products obtained by expressing peroxidases may differ from plant to plant.

Additionally, resistance to corn earworms is negatively correlated to silk browning indicating that an increase in peroxidase would lower resistance (Byrne et al., *Environ. Entomol.* 18:356–360 (1989)). This teaches away from using peroxidase to control insects in monocots.

Further, altered lignin production in corn (in bm mutants) causes increased susceptibility to insects (Barriere and Argillier, *Agronomie* 13:865–876 (1993)). Thus, a foreign peroxidase which alters lignification would not be expected to decrease susceptibility to insects. Further, it was unexpected from the teachings of Bergvinson et al., *The Canadian Entomologist* 127:111–122 (January/February 1995) that insect resistance is imparted to plants by toughening of tissues due to peroxidase activity in the early stages of growth.

Therefore, prior to the present invention, the effect of expressing a recombinant peroxidase in monocots was unpredictable.

BRIEF SUMMARY OF THE INVENTION

Methods for controlling insects and insect resistant monocot plants are provided.

The invention, more specifically, provides a method for controlling insects comprising feeding or contacting an insect with an insecticidal amount of transgenic monocotyledonous plant cells comprising recombinant DNA comprising a coding sequence encoding peroxidase, wherein expression of peroxidase confers insect resistance in the transgenic monocotyledonous plant cells.

The invention also provides a fertile transgenic monocotyledonous plant comprising recombinant DNA comprising a coding sequence encoding peroxidase, wherein expression of peroxidase confers on the monocotyledonous plant a phenotypic trait.

The invention also provides a transgenic plant cell, tissue, or seed obtained from the above-described plant.

The invention further provides transgenic descendants of the above-described plant.

The invention also provides a transgenic plant cell, tissue, or seed obtained from the above-described descendants.

Further objects and advantages of the present invention will be clear from the description that follows.

BRIEF DESCRIPTION OF THE DRAWINGS

FIG. 1. The plasmid, pJS20293, is shown as containing tobacco anionic peroxidase inserted between (1) the CaMV 35S promoter linked to the shrunken intron and (2) the CaMV 35S terminator.

FIG. 2. The plasmid, pUBIAc, is shown.

DEFINITIONS

Plant cell: the structural and physiological unit of plants, consisting of a protoplast and the cell wall. The term "plant cell" refers to any cell which is either part of or derived from a plant. Some examples of cells include differentiated cells that are part of a living plant; differentiated cells in culture; undifferentiated cells in culture; the cells of undifferentiated tissue such as callus or tumors; differentiated cells of seeds, embryos, propagules and pollen.

Plant Tissue: a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

Protoplast: a plant cell without a cell wall.

Descendant plant: a sexually or asexually derived future generation plant which includes, but is not limited to, progeny plants.

Transgenic plant: a plant having stably incorporated recombinant DNA in its genome.

Recombinant DNA: Any DNA molecule formed by joining DNA segments from different sources and produced using recombinant DNA technology.

Recombinant DNA technology—Technology which produces recombinant DNA in vitro (or in vivo) and transfers the recombinant DNA into cells where it can be expressed or propagated (See, Concise Dictionary of Biomedicine and Molecular Biology, Ed. Juo, CRC Press, Boca Raton (1996)), for example, transfer of DNA into a protoplast(s) or cell(s) in various forms, including, for example, (1) naked DNA in circular, linear or supercoiled forms, (2) DNA contained in nucleosomes or chromosomes or nuclei or parts thereof, (3) DNA complexed or associated with other molecules, (4) DNA enclosed in liposomes, spheroplasts, cells or protoplasts or (5) DNA transferred from organisms other than the host organism (ex. *Agrobacterium tumefaciens*). These and other various methods of introducing the recombinant DNA into cells are known in the art and can be used to produce the transgenic cells or transgenic plants of the present invention.

Recombinant DNA technology also includes the homologous recombination methods described in Treco et al., WO 94/12650 and Treco et al., WO 95/31560 which can be applied to increasing peroxidase activity in a monocot. Specifically, regulatory regions (ex. promoters) can be introduced into the plant genome to increase the expression of the endogenous peroxidase.

Also included as recombinant DNA technology is the insertion of a peroxidase coding sequence lacking selected expression signals into a monocot and assaying the transgenic monocot plant for increased expression of peroxidase due to endogenous control sequences in the monocot. This would result in an increase in copy number of peroxidase coding sequences within the plant.

The initial insertion of the recombinant DNA into the genome of the $R^0$ plant is not defined as being accomplished by traditional plant breeding methods but rather by methods as described herein. However, following the initial insertion, transgenic descendants can be propagated using traditional breeding methods.

Chimeric gene: A DNA molecule containing at least two heterologous parts, e.g., parts derived from pre-existing DNA sequences which are not associated in their pre-existing states, these sequences having been preferably generated using recombinant DNA technology.

Expression cassette: a DNA molecule comprising a promoter and a terminator between which a coding sequence can be inserted.

Coding sequence: a DNA molecule which, when transcribed and translated, results in the formation of a polypeptide or protein.

Gene: a discrete chromosomal region comprising a regulatory DNA sequence responsible for the control of expression, i.e. transcription and translation, and of a coding sequence which is transcribed and translated to give a distinct polypeptide or protein.

Phenotypic trait: an observable property resulting from the expression of one or more genes.

DETAILED DESCRIPTION OF THE INVENTION

The present invention relates to methods for controlling insects.

Any method wherein expression of peroxidase confers insect resistance in monocotyledonous plant cells is encompassed by the present invention.

In one preferred embodiment, the present invention relates to a method for controlling insects comprising feeding or contacting an insect with an insecticidal amount of transgenic monocotyledonous plant cells comprising recombinant DNA comprising a coding sequence encoding peroxidase, wherein expression of peroxidase confers insect resistance in the transgenic monocotyledonous plant cells.

In a further preferred embodiment, the homologous recombination methods described in Treco et al., WO 94/12650 and Treco et al., WO 95/31560 are used to increase peroxidase activity in a monocot and thus, insect resistance. Specifically, regulatory regions (ex. promoters) are introduced into the plant genome to increase the expression of the endogenous peroxidase which increases the insect resistance of the plant.

In another preferred embodiment, the present invention relates to the insertion of a peroxidase coding sequence lacking selected expression signals into a monocot and assaying the transgenic monocot plant for increased expression of peroxidase due to endogenous control sequences in the monocot. This results in an increase in copy number of peroxidase coding sequences within the plant.

In a further preferred embodiment, the present invention relates to a method of increasing the copy number of the endogenous peroxidase gene wherein insect resistance is conferred on the monocot plant. Such a method is preferably accomplished using traditional plant breeding methods or using tissue culture techniques.

Insect resistant plants comprise increased insect resistance over that found in native non-manipulated plants due to increased levels of peroxidase.

Insect Resistance

Preferably, the transgenic monocots of the present invention are resistant to insects selected from the orders including but not limited to Coleoptera, Diptera, Hymenoptera, Lepidoptera, Mallophaga, Homoptera, Hemiptera, Orthroptera, Thysanoptera, Dermaptera, Isoptera, particularly, Coleoptera and Lepidoptera. For purposes of the present invention, it is recognized that the transgenic plants of the invention can be resistant to not only insects but also fungi, bacteria, nematodes, mites, and the like.

Maize plants of the present invention are preferably resistant to an insect or insects selected from the group which includes but is not limited to *Ostrinia nubilalis,* European corn borer; *Sesemia nonegrioides,* stalk corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* sugarcane borer, *Diabrotica virgifera virgifera,* western corn rootworm, *Diabrotica longicornis barberi,* northern corn rootworm, *Diabrotica undecimpunctata howardi,* southern corn rootworm, *Melanotus spp.,* wireworms, *Cyclocephala borealis,* northern masked chafer (white grub), *Cyclocephala immaculata,* southern masked chafer (white grub), *Popillia japonica,* Japanese beetle (grub and adult forms), *Chaetocnema pulicaria,* corn flea beetle, *Sphenophorus maidis,* maize billbug, *Rhopalosiphum maidis,* corn leaf aphid, *Anuraphis maidiradicis,* corn root aphid, *Blissus leucopterus leucopterus,* chinch bug, *Melanoplus femurrubrum,* redlegged grasshopper, *Melanoplus sanguinipes,* migratory grasshopper, *Hylemya platura,* seedcorn maggot, *Agromyza parvicornis,* corn blotch leafminer, *Anaphothrips obscurus,* grass thrips, *Solenopsis milesta,* thief ant, and *Tetranychus urticae,* two-spotted spider mite.

Sorghum plants of the present invention are preferably resistant to an insect or insects selected from the group which includes but is not limited to *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranean,* granulate cutworm; *Phyllophaga crinita,* white grub; *Eleodes, Conoderus,* and *Aeolus spp.,* wireworms; *Oulema melanopus,* cereal leaf beetle; *Chaetocnema pulicaria,* corn flea beetle; *Sphenophorus maidis,* maize billbug; *Rhopalosiphum maidis,* corn leaf aphid; *Sipha flara,* yellow sugarcane aphid; *Blissus leucopterus leucopterus,* chinch bug; *Contarinia sorghicola,* sorghum midge; *Tetranychus cinnabarinus,* carmine spider mite; and *Tetranychus urticae,* twospotted spider mite.

Wheat plants of the present invention are preferably resistant to an insect or insects selected from the group which includes but is not limited to *Pseudaletia unipunctata,* army worm; *Spodoptera frugiperda,* fall armyworm; *Elasmopalpus lignosellus,* lesser cornstalk borer; *Agrotis orthogonia,* pale western cutworm; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; and *Aceria tulipae,* wheat curl mite.

Rice plants of the present invention are preferably resistant to an insect or insects selected from the group which includes but is not limited to *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus leucopterus,* chinch bug; and *Acrosternum hilare,* green stink bug.

Barley plants of the present invention are preferably resistant to an insect or insects selected from the group which includes but is not limited to *Ostrinia nubilalis,* European corn borer; *Agrotis ipsilon,* black cutworm; *Schizaphis graminum,* greenbug; *Blissus leucopterus leucopterus,* chinch bug; *Acrosternum hilare,* green stink bug; *Euschistus servos,* brown stink bug; *Hylemya platura,* seedcorn maggot; *Mayetiola destructor,* Hessian fly; Thysanoptera, Thrips; and *Petrobia latens,* brown wheat mite.

Monocotyledonous Plants

In one embodiment, the present invention relates to a fertile transgenic monocotyledonous plant (monocot) comprising recombinant DNA comprising a coding sequence encoding peroxidase.

Monocots are plants whose embryo has one cotyledon. Monocots are one of the two large classes of angiosperms (dicots being the other large class).

Preferred families within the monocot class include: gramineae (grass family; preferred members of the gramineae include forage grasses (ex. Festuca (fescue grass)), Hordeum (barley), Avena (oat), *Zea mays* (corn), Triticum (wheat), Secale (rye), *Sorgum vulgare* (sorghum), and *Oryza sativa* (rice)); liliaceae (lily family; preferably Allium (onion) and Asparagus); and Dioscoreaceae (yam family). The present invention also includes but is not limited to monocot species, for example, preferred lines of *Zea mays* include Funk 5N984, Funk 5N986, Funk 2717, Funk 211D, Funk 2N217A, B73, A632, CM105, B37, B84, B14, Mo17, A188, CG00526, CG00615 and CG00714.

In another embodiment, the present invention relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Peroxidase Coding Sequences

As described herein, the present invention relates to a fertile transgenic monocot plant transformed with a peroxidase coding sequence. Preferably, the peroxidase coding sequence confers on the monocot plant a phenotypic trait that is not found in a parent plant lacking the peroxidase coding sequence or its overexpression. Phenotypic traits which can be produced include insect resistance and enhanced standability.

More preferably, the peroxidase coding sequence in the transgenic plant is sexually transmitted. In one preferred embodiment, the peroxidase coding sequence is sexually transmitted through a complete normal sexual cycle of the R0 plant to the R1 generation. Additionally preferred, the peroxidase coding sequence is expressed so that the level of peroxidase in the cells, tissues, seeds or plant is increased above the level in the cells, tissues, seeds or plant of a monocot which only differ in that the peroxidase coding sequence is absent.

In one preferred embodiment, the peroxidase coding sequence is an anionic, cationic, or neutral peroxidase coding sequence. In another preferred embodiment, the peroxidase is a guaiacol peroxidase, NADH peroxidase, cytochrome-C peroxidase, catalase, glutathione peroxidase, L-ascorbate peroxidase, manganese peroxidase, hydrogen peroxide generating peroxidase, and/or lignin forming peroxidase.

A variety of peroxidase coding sequences are available in the art and are available for use in the present invention. For example, peroxidases have been cloned from tobacco (Lagrimini, M., et al., *Proc. Natl. Acad. Sci. USA* 84:7542–7546 (1987), potato (Roberts et al., *Plant Molecular Biology* 11:5–26 (1988)), horseradish (Fujiyama et al., *European Journal of Biochemistry*, 173, 681–687 (1988); Fujiyama et al., *Gene* 89:163–169 (1990); and Welinder, K. G., *European Journal of Biochemistry* 96:483–502 (1979)), tomato (Roberts, E. and Kolattukudy, P. E., *Molecular Genes and Genetics,* 217, 223–232 (1989)), peanut (Buffard et al., *Proc. Natl. Acad. Sci. USA* 87:8874–8878 (1990)), cucumber (Morgens et al., *Plant Molecular Biology* 14:715–725 (1990)), *Arabidopsis* (Intapruk et al., *Gene* 98:237–241 (1991)), wheat (Hertig et al., *Plant Molecular Biology* 16:171–174 (1991); and Rebmann et al., *Plant Molecular Biology* 16:329–331 (1991)), barley (Rasmussen et al., *Plant Molecular Biology* 16:317–327 (1991); and Theilade, B. and Rasmussen, S. K, *Gene* 118:261–266 (1992)), rice (Reimman et al., *Plant Physiology* 100:1611–1612 (1992)), maize (Hwang, Ph.D. thesis, Ohio State University), and turnip (Mazza and Welinder, *European Journal of Biochemistry* 108:481–489 (1980)).

The peroxidase coding sequences used in the present invention are not to be limited to known peroxidase coding sequences. Novel peroxidase coding sequences for use in the invention can be isolated by identity or similarity with known sequences. The tobacco anionic peroxidase shows identity or similarity with the amino acid sequences of the horseradish cationic peroxidase and the turnip cationic peroxidase. The overall identity or similarity between tobacco and horseradish is 52%; for tobacco and turnip, the peroxidases have 46% identity or similarity. Furthermore, there are regions in the peroxidase coding sequence where the identity or similarity approaches 100%. Four of these conserved regions correspond to domains critical for general peroxidase activity. Accordingly, DNA sequences from the conserved regions can be utilized to generally clone peroxidase coding sequences from any plant species using methods well known in the art (See, for example, Current Protocols in Molecular Biology, eds.: Ausubel et al., John Wiley & Sons, Inc., New York, N.Y. (Spring 1996)).

Likewise, novel peroxidase coding sequences can be isolated using antibodies made against one peroxidase enzyme to isolate other peroxidase enzymes. Homology between the various peroxidase isozymes has been demonstrated with antibodies made to the tobacco anionic peroxidase. By immunoblot analysis these antibodies cross-reacted strongly with the horseradish and turnip isozymes and also cross-reacted with most of the other tobacco isozymes. See, Lagrimini, M., et al., *Proc. Natl. Acad. Sci. USA* 84:7542–7546 (1987). The novel peroxidase enzymes can be sequenced using methods well known in the art and their corresponding coding sequences can be isolated using methods well known in the art (For example see, Sambrook et al. Molecular Cloning-A Laboratory Manual, 2nd edition, Cold Spring Harbor Laboratory Press, NY, USA (1988)).

The transgenic expression in plants of peroxidase coding sequences derived from sources other than the host plant (for example, from bacterial sources) can require the modification of those coding sequences to achieve and optimize their expression in the host plant. In some cases, modification to the coding sequences and adjacent sequence will not be required. It is sufficient to isolate a fragment containing the coding sequence of interest and to insert it downstream of a plant promoter. For example see, Gaffney et al., *Science* 261: 754–756 (1993). Preferably, as little adjacent microbial sequence should be left attached upstream of the ATG and downstream of the stop codon.

The peroxidase coding sequence can be optimized for enhanced expression in the host monocot. For example, since the preferred codon usage and codon frequency in the host plant can differ from the usage and frequency of the peroxidase coding sequence of interest, comparison of the usage and frequency of codons within a cloned coding sequence to the usage and frequency in plant coding sequences (and in particular coding sequences from the target plant) enables an identification of the codons within the coding sequence which can preferably be changed. The preferred codons can be determined from the codons of highest frequency in the proteins expressed in the largest amount in the plant or from the codons most preferred in the plant. See, for example, Adang et al., EPO 359472; Fischhoff et al., EPO 385962; Cornelissen et al., WO 91/16432; Koziel et al., WO 93/07278; Perlak et al., *Proc. Natl. Acad. Sci. USA* 88:3324–3328 (1991); and Murray et al., *Nucleic Acids Research* 17:477–498 (1989).

In this manner, the nucleotide sequences can be optimized for expression in the specific plant of interest. It is recognized that all or any part of the coding sequence can be optimized or synthetic. That is, synthetic or partially optimized sequences can also be used.

Plants differ from microorganisms in that their messages do not possess a defined ribosome binding site. Rather, ribosomes attach to the 5' end of the message and scan for the first available ATG at which to start translation. In plants, there is a preference for certain nucleotides adjacent to the ATG and thus, expression of microbial genes can be enhanced by the inclusion of a eukaryotic consensus translation initiator at the ATG. Clontech (1993/1994 catalog, page 210) have suggested a sequence as a consensus translation initiator for the expression of the E. coli uidA gene in plants. Further, Joshi, *Nucl. Acid Res.* 15: 6643–6653 (1987) has compared many plant sequences adjacent to the ATG and also suggests a consensus sequence. In situations where difficulties are encountered in the expression of microbial coding sequences in plants, inclusion of one of these sequences at the initiating ATG is preferred.

Coding sequences cloned from non-plant sources can also contain motifs which can be recognized in plants as 5' or 3' splice sites, thus generating truncated or deleted messages. These sites can be removed using the techniques known in the art (See, for example, Current Protocols in Molecular Biology, eds.: Ausubel et al., John Wiley & Sons, Inc., New York, N.Y. (Spring 1996)).

Plant Gene Construction

A recombinant DNA comprising a coding sequence encoding a peroxidase can be used for producing transgenic plant tissues. A plant is preferably transformed with at least one recombinant DNA which can further comprise a transcriptional initiation region and a promoter both of which are operably linked to the peroxidase coding sequence.

The transcriptional initiation regions can be native or foreign to the host. By foreign it is intended that the transcriptional initiation region is not found in the wild type host into which the transcriptional initiation region is introduced.

The termination region can be obtained from (1) the same gene from which the transcriptional initiation region was obtained, (2) the peroxidase gene used or (3) derived from other source.

The peroxidase coding sequence is preferably operably fused to a plant expressible promoter, preferable promoters include constitutive, inducible, temporally regulated, developmentally regulated, chemically regulated, tissue-preferred and/or tissue-specific promoters. In one preferred embodiment, the peroxidase coding sequence is operably linked to its naturally occuring promoter and/or polyadenylation signal sequence.

Preferred constitutive promoters include the CaMV 35S and 19S promoters (Fraley et al., U.S. Pat. No. 5,352,605). An additionally preferred promoter is derived from any one of several of the actin genes, which are known to be expressed in most cell types. The promoter expression cassettes described by McElroy et al., *Mol Gen. Genet.* 231: 150–160 (1991) can be easily modified for the expression of the peroxidase coding sequence and are particularly suitable for use in monocotyledonous hosts.

Yet another preferred constitutive promoter is derived from ubiquitin, which is another gene product known to accumulate in many cell types. The ubiquitin promoter has been cloned from several species for use in transgenic plants (e.g. sunflower—Binet et al. Plant Science 79: 87–94 (1991), maize—Christensen et al. Plant Molec. Biol. 12: 619–632 (1989)). The maize ubiquitin promoter has been developed in transgenic monocot systems and its sequence and vectors constructed for monocot transformation are disclosed in Christiansen et al., EP 0 342 926. The ubiquitin promoter is suitable for the expression of the peroxidase coding sequence in transgenic plants, especially monocotyledons.

Tissue-specific or tissue-preferential promoters useful for the expression of the peroxidase coding sequence in plants, particularly maize, are those which direct expression in root, pith, leaf or pollen. Such promoters are disclosed in Koziel et al., WO 93/07278. Chemically inducible promoters useful for directing the expression of the peroxidase coding sequence in plants are also preferred (See, Alexander et al., WO 95/19443).

In addition to promoters, a variety of transcriptional terminators are also available for use in chimeric gene construction using a peroxidase coding sequence. Transcriptional terminators are responsible for the termination of transcription beyond the transgene and its correct polyadenylation. Appropriate transcriptional terminators and those which are known to function in plants include the CaMV 35S terminator, the tml terminator, the pea rbcS E9 terminator and others known in the art. Convenient termination regions are available from the Ti-plasmid of *A. tumefaciens*, such as the octopine synthase and nopaline synthase termination regions. See also, Rosenberg et al., *Gene,* 56:125 (1987); Guerineau et al., *Mol. Gen. Genet.,* 262:141–144 (1991); Proudfoot, Cell, 64:671–674(1991); Sanfacon et al., *Genes Dev.,* 5:141–149; Mogen et al., *Plant Cell,* 2:1261–1272 (1990); Munroe et al., Gene, 91:151–158 (1990); Ballas et al., *Nucleic Acids Res.* 17:7891–7903 (1989); Joshi et al., *Nucleic Acid Res.,* 15:9627–9639 (1987)).

Numerous sequences have also been found to enhance gene expression from within the transcriptional unit and these sequences can be used in conjunction with the peroxidase coding sequence to increase expression in transgenic plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., *Genes Develop.* 1: 1183–1200 (1987)). Intron sequences have been routinely incorporated into plant transformation vectors, typically within the non-translated leader.

The construct can also include a regulator such as a nuclear localization signal (Kalderon et al. *Cell* 39:499–509 (1984); and Lassner et al., *Plant Molecular Biology* 17:229–234 (1991)), plant translational consensus sequence (Joshi, C. P., *Nucleic Acids Research* 15:6643–6653 (1987)), an intron (Luehrsen and Walbot, *Mol. Gen. Genet.* 225:81–93 (1991)), and the like, operably linked to the appropriate nucleotide sequence.

Preferably, the 5' leader sequence is included in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, *Proc. Natl. Acad. Sci. USA* 86:6126–6130 (1989)); potyvirus leaders, for example, TEV leader (Tobacco Etch Virus) (Allison et al., MDMV leader (Maize Dwarf Mosaic Virus); *Virology,* 154:9–20 (1986)), and human immunoglobulin heavy-chain binding protein (BiP), (Macejak, D. G., and Sarnow, P., *Nature* 353:90–94 (1991); untranslated leader from the coat protein mRNA of alfalfa mosaic virus (AMV RNA 4)(Jobling, S. A., and Gebrke, L., *Nature,* 325:622–625 (1987)); tobacco mosaic virus leader (TMV)(Gallie, D. R. et al., *Molecular-Biology* of RNA, pages 237–256(1989)); and maize chlorotic mottle virus leader (MCMV) (Lommel, S. A. et al., *Virology* 91:382–385 (1991)). See also, Della-Cioppa et al., *Plant Physiology* 84:965–968 (1987).

In preparing the recombinant DNA, various DNA fragments can be manipulated, so as to provide for the DNA sequences in the proper orientation and, as appropriate, in the proper reading frame. Towards this end, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions, e.g. transitions and transversions, are involved.

Plant Vectors

Numerous transformation vectors are available for plant transformation, and the peroxidase coding sequences can be used in conjunction with any such vectors. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., *Nucl Acids Res.* 18: 1062 (1990), Spencer et al., *Theor. Appl. Genet.* 79: 625–631(1990)), the hph gene which confers resistance to the antibiotic hygromycin (Blochinger & Diggelmann, *Mol. Cell. Biol.* 4: 2929–2931), and the dhfr gene, which confers resistance to methotrexate (Bourouis et al, EMBO J 2: 1099–1104 (1983)).

Many vectors are available for transformation using *Agrobacterium tumefaciens*. These typically carry at least one T-DNA border sequence and include vectors such as pBIN19 (Bevan, *Nucl. Acids Res.* 12(22): 8711–8721 (1984)). In one preferred embodiment, the peroxidase coding sequence can be inserted into either of the binary vectors pCIB200 and pCIB2001 for use with Agrobacterium. These vector cassettes for Agrobacterium-mediated transformation can be constructed in the following manner. pTJS75kan was created by NarI digestion of pTJS75 (Schmidhauser & Helinski, *J Bacteriol.* 164: 446–455 (1985)) allowing excision of the tetracycline-resistance gene, followed by insertion of an AccI fragment from pUC4K carrying an NPTII (Messing & Vierra, *Gene* 19: 259–268 (1982); Bevan et al., *Nature* 304: 184–187 (1983); McBride et al., *Plant Molecular Biology* 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., *Gene* 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

An additional vector useful for Agrobacterium-mediated transformation is the binary vector pCIB10 which contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al, *Gene* 53: 153–161 (1987). Various derivatives of pCIB10 have been constructed which incorporate the gene for hygromycin B phosphotransferase described by Gritz et al., *Gene* 25: 179–188 (1983). These derivatives enable selection of transgenic plant cells on hygromycin only (pCIB743), or hygromycin and kanamycin (pCIB715, pCIB717).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in Koziel et al., WO 93/07278. The gene providing resistance to phosphinothricin is the bar gene from *Streptomyces hygroscopicus* (Thompson et al., *EMBO J* 6: 2519–2523 (1987)). This vector is suitable for the cloning of plant expression cassettes containing their own regulatory signals.

An additional transformation vector is pSOG35 which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp; see Dennis et al., *Nucleic Acid Res.* 12:3983–4000 (1984)) and 18 bp of the GUS untranslated leader sequence (see Jefferson et al., *Proc. Nat. Acad. Sci. USA* 83: 8447–8451 (1986). A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Transformation Techniques

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., *BioTechniques* 4:320–334 (1986)), electroporation (Riggs et al., *Proc. Natl. Acad. Sci. USA* 83:5602–5606 (1986), Agrobacterium-mediated transformation (Hinchee et al., Biotechnology 6:915–921 (1988); See also, Ishida et al., *Nature Biotechnology* 14:745–750 (June 1996) for maize transformation), direct gene transfer (Paszkowski et al., *EMBO J* 3:2717–2722 (1984); Hayashimoto et al., *Plant Physiol.* 93:857–863 (1990)(rice)), and ballistic particle acceleration using devices available from Agracetus, Inc., Madison, Wis. and Dupont, Inc., Wilmington, Del. (see, for example, Sanford et al., U.S. Pat.

No. 4,945,050; and McCabe et al., *Biotechnology* 6:923–926 (1988)). See also, Weissinger et al., *Annual Rev. Genet.* 22:421–477 (1988); Sanford et al., *Particulate Science and Technology* 5:27–37 91987)(onion); Svab et al., *Proc. Natl. Acad. Sci. USA* 87: 8526–8530 (1990) (tobacco chloroplast); Christou et al., *Plant Physiol.* 87:671–674 (1988)(soybean); McCabe et al., *Bio/Technology* 6:923–926 (1988)(soybean); Klein et al., *Proc. Natl. Acad. Sci. USA,* 85:4305–4309 (1988)(maize); Klein et al., Bio/Technology 6:559–563 (1988) (maize); Klein et al., *Plant Physiol.* 91:440–444 (1988) (maize); Fromm et al., *Bio/Technology* 8:833–839 (1990); and Gordon-Kamm et al., *Plant Cell* 2: 603–618 (1990) (maize); Koziel et al., *Biotechnology* 11: 194–200 (1993)(maize); Shimamoto et al., Nature 338: 274–277 (1989) (rice); Christou et al., *Biotechnology* 9: 957–962 (1991) (rice); Datta et al., *Bio/Technology* 8:736–740 (1990) (rice); European Patent Application EP 0 332 581 (orchardgrass and other Pooideae); Vasil et al., *Biotechnology* 11: 1553–1558 (1993) (wheat); Weeks et al., *Plant Physiol.* 102: 1077–1084 (1993) (wheat); Wan et al., *Plant Physiol.* 104: 37–48 (1994)(barley); Jahne et al., *Theor. Appl. Genet.* 89:525–533 (1994)(barley); Umbeck et al., Bio/Technology 5: 263–266 (1987)(cotton); Casas et al., *Proc. Natl. Acad. Sci. USA* 90:11212–11216 (December 1993)(sorghum); Somers et al., *Bio/Technology* 10:1589–1594 (December 1992)(oat); Torbert et al., *Plant Cell Reports* 14:635–640 (1995)(oat); Weeks et al., *Plant Physiol.* 102:1077–1084 (1993)(wheat); Chang et al., WO 94/13822 (wheat) and Nehra et al., *The Plant Journal* 5:285–297 (1994)(wheat).

One particularly preferred set of embodiments for the introduction of recombinant DNA molecules into maize by microprojectile bombardment can be found in Koziel et al., *Biotechnology* 11: 194–200 (1993), Hill et al., *Euphytica* 85:119–123 (1995) and Koziel et al., *Annals of the New York Academy of Sciences* 792:164–171 (1996). An additional preferred embodiment is the protoplast transformation method for maize as disclosed in Shillito et al., EP 0 292 435.

Transformation of plants can be undertaken with a single DNA species or multiple DNA species (i.e. co-transformation) and both these techniques are suitable for use with the peroxidase coding sequence.

Methods using either a form of direct gene transfer, particle gun technology or Agrobacterium-mediated transfer usually, but not necessarily, are undertaken with a selectable or screenable marker which provide resistance to an antibiotic (e.g., kanamycin, hygromycin or methotrexate) or a herbicide (e.g., phosphinothricin). The choice of selectable or screenable marker for plant transformation is not, however, critical to the invention.

Multiple Peroxidase Coding Sequences and the Combination of Peroxidase with Other Insecticidal Compounds The peroxidase coding sequence is preferably used alone or in combination. That is, one or more peroxidase coding sequence can be inserted into a plant to control different insect pests. This can be accomplished by (1) transforming a host plant with a DNA sequence comprising more than one peroxidase coding sequence, (2) transforming a host plant with a DNA sequence comprising a single peroxidase coding sequence and identifying multiple insertions of the DNA sequence into the host genome, or (3) repeated transformation of a host plant with a peroxidase coding sequence until the host plant comprises the desired number of peroxidase coding sequences.

The level of insect protection of a plant against a given insect and/or its spectrum of insecticidal activities can also be increased by combining a peroxidase coding sequence with other coding sequences encoding proteins capable of controlling insects.

*Bacillus thuringiensis* (Bt) is a gram-positive, spore-forming bacterium which produces a parasporal crystal during sporulation (For review see, Koziel et al., *Biotech. and Gen. Engin. Reviews* 11:171–228 (1993)). These crystals are predominantly comprised of one or more porteins, called δ-endotoxins or insecticidal crystal proteins, known to possess insecticidal activity when ingested by certain insects. Numerous strains of Bt are currently known. Each strain produces differing numbers of δ-endotoxins with various insecticidal activities. Examples of Bt endotoxins which can be used in combination with peroxidases include, but are not restricted to CryIA(b) (Koziel et al., *Bio/Technology* 11: 194–200 (1993)), CryIA(c) (U.S. Pat. No. 5,530,197), Cry1H (also called Cry9C) (Lambert et al. *Appl. Environ. Microbiol.* 62: 80–86 (1996)), and CryIIIA (Adang et al. *Plant Mol. Biol.* 21: 1131–1145 (1993).

Pesticidal proteins produced during vegetative growth of Bacillus strains (vegetative insecticidal proteins, VIPs) can also be used in combination with peroxidases. For examples of VIPs see, Warren et al., WO 94/21795; Warren et al., WO 96/10083; and Estruch et al., *Proc. Natl. Acad. Sci. USA* 93: 5389–5394 (1996).

Examples of other proteins with insecticidal compounds which can be used in combination with peroxidases include, but are not restricted to, cholesterol oxidases (U.S. Pat. No. 5,518,908), protease inhibitors, lectins, and α-amylases.

Monocots expressing more than one insect resistance coding sequence can made by any method known in the art. For example, the peroxidase coding sequence can be used to transform a monocot at the same time as another insect principle gene (cotransformation), the second insect principle gene can be introduced into a plant which has already been transformed with a peroxidase coding sequence, or by vice versa, or alternatively, transgenic plants, one expressing a peroxidase coding sequence and one expressing a second insect principle can be crossed to bring the coding sequences together in the same plant.

The present invention is described in further detail in the following non-limiting examples. In the Examples, procedures for making, manipulating and analyzing nucleic acids were/are carried out by standard procedures as described in Sambrook et al. Molecular Cloning-A Laboratory Manual, 2nd edition, Cold Spring Harbor Laboratory Press, NY, USA (1988).

EXAMPLE 1

Transgenic Maize Plants Comprising a Peroxidase Coding Sequence

Vector Construction pPOD$_{3.5}$ (Lagrimini et al., *Proc. Natl. Acad. Sci* 84: 438–442 (1987)) contains the 1256-bp tobacco anionic peroxidase cDNA which comprises the entire peroxidase coding sequence, including a 22-amino acid signal peptide which facilitates secretion into the cell wall space. pPOD$_{3.5}$ was digested with BamHI and cloned into the BamHI sites of pCIB710 (Rothstein et al., *Gene* 53:153–161(1987)). This new construct was digested with EcoRI and subcloned into Bluescript SK+ (Stratagene Catalogue, 1994)—the resulting construct designated as pJS20293 (FIG. 1) was placed on deposit under the terms of the Budapest Treaty with the Agricultural Research Culture Collection (NRRL) International Depositary Authority, 1815 N. University Street, Peoria Ill. 61604 U.S.A. on Sep. 27, 1996 as NRRL B-21626. pJS20293 contains the 1200 bp peroxidase cDNA clone behind the CaMV 35S promoter and the shrunken intron (Werr et al., *EMBO J.* 4: 1373–1380 (1985)) followed by the CaMV 35S terminator in a BlueScript (Stratagene) plasmid (FIG. 1). pJS20293 was cotransformed with pUBI/Ac (FIG. 2), a plasmid containing a chimeric bar gene coding for resistance to phosphinothricin.

Transformation Using Immature Zygotic Embryos

In two separate experiments, 600 immature embryos of CG00526, a Lancaster-type inbred, were aseptically excised 12–13 days after pollination from surface-sterilized greenhouse-grown ears. Embryos 1.5 to 20 mm in size were plated with the scutellum up on callus initiation medium, 2DG4+5mg/l chloramben. 2DG4 medium is Duncan's (Duncan et al., *Planta* 165:322–332 (1985)) "D" medium modified to contain 20 mg/L glucose.

pJS20293 DNA was precipitated onto 1 $\mu$m gold microcarrier as described by the Dupont Biolistic manual. The DNA/gold mixture was prepared so as to deliver approximately 1 $\mu$g of pJS20293 DNA per bombardment. For the immature embryo transformation, 6.34 $\mu$g of pJS20293+ 7.21 $\mu$g of pUBI/Ac were used per 50 $\mu$l of microcarrier. Both preparations were brought to 85 $\mu$l with ethanol and 10 $\mu$l of each were dried onto macrocarriers.

Four hours prior to bombardment the embryos were transferred to 12DG4+5 mg/L chloramben for osmotic treatment. Thirty-six embryos on a plate were bombarded using the PDS-1000He Biolistics device according to the manufacture's directions (Dupont). The embryos were arranged on the target plate around a 2 cm diameter circle at the center of the plate with the coleorhizal ends of the scutellum all oriented in the same direction. The target plates were then angled upwards at a 30° angle so that the coleorhizal ends were hit first by the particle spray. A 24×24 $\mu$m standard screen supplied by the Biolistic manufacturer was used with rupture discs of 1550 psi value for the bombardments. Three hours following bombardment embryos were returned to 2DG4+5 mg/L chloramben media and then cultured in the dark at 25° C.

Fourteen days after bombardment, embryogenic responses were transferred to callus maintenance media 2DM4+0.5 mg/L 2,4-dichlorophenoxyacetic acid (2,4-D). M4 media is the same as G4 minus casamino acids. This media contained 5 mg/L Basta® were gradually increased to 20 mg/L.

Regeneration was initiated after 12 weeks on Basta® selection. Type I callus was subcultured onto a modified Murashige and Skoog medium (MS) (Murashige and Skoog, *Physiologia Plantarum* 15:473–497 (1962)) containing 3% sucrose, 0.25 mg/L 2,4-D, 5 mg/l benzylzminopurine and 5 mg/l Basta® and cultured under 16 hours of light (50 $\mu$E/m-2/s-1), 8 hours dark, 25° C. Two weeks later the tissue was transferred to MS medium containing 3% sucrose and 5 mg/l Basta®. Regenerated plants were grown on MS medium modified to contain ½ the concentration of salts and 3% sucrose in GA7 containers.

Transformation Using Type I Embryogenic Callus

For transformation of maize using Type I embryogenic callus, the callus was obtained from immature zygotic embryos using standard culture techniques. For gene delivery, approximately 300 mg of the Type I callus was prepared by either chopping with a scalpel blade or by subculturing 3–5 days prior to gene delivery. Prior to gene delivery, the prepared callus was placed onto semi-solid culture medium again containing 12% sucrose. After approximately 4 hours, the tissue was bombarded with pJS20293 using the PDS-1000/He Biolistic device from BioRad. Two $\mu$g pJS20293 was precipitated onto 1 $\mu$m gold particles using essentially the standard protocol from Bio-Rad. Approximately 16 hours after gene delivery the callus was transferred to standard culture medium containing 2% sucrose and 1 mg/L phosphinothricin. The callus was subcultured on selection for 8 weeks, after which surviving and growing callus was transferred to standard regeneration medium for the production of plants. The regenerated plants were assayed for resistance to European corn borer. Resistant plants were obtained.

The resulting transgenic plants were used in a conventional plant breeding scheme to produce more transgenic plants with similar insecticidal properties. The transgenic plants were also crossed with other varieties of the same plant. The transgenic plants also produced seeds which contained the chimeric peroxidase gene stably inserted in their genome.

Transgenic maize plants containing the peroxidase coding sequence were identified by Southern blot analysis. When genomic DNA from transgenic plants was digested with the EcoRI restriction enzyme, a band of approximately 1.3 Kb was detectable using the peroxidase gene as specific probe signaling the presence of an intact peroxidase gene.

Transgenic maize expressing the peroxidase coding sequence were also identified by northern blot analysis. A band of approximately 1.2 Kb in size was observed in the RNA blot when hybridized with a peroxidase specific probe.

Insect Bioassay

A total of 46 transgenic maize plants were originally evaluated for insecticidal activity against *Ostrinia nubilalis* (ECB). This first group of bioassays was performed by applying 10 first instar ECB larvae to a leaf cutting that had been placed into a Gelman petri dish with a moistened filter pad to prevent the leaf cutting from drying out. The larvae were allowed to feed undisturbed for two days. Two plants from event 554 were positive in the preliminary bioassay. These two plant samples showed no signs of insect feeding and the larvae were dead. The remainder of the plants in that event and other events had healthy feeding insects.

With this activity noted, more repetitions were performed in the next ECB bioassay. Four repetitions with five larvae per repetition were done. A percent mortality reading was taken after two days. Since the plants still appeared to contain insecticidal activity, it was decided to test them against other target insects.

Transgenic maize plants expressing the peroxidase enzyme were assayed for insecticidal activity by means of insect bioassays. The procedure is similar for any maize plant transformed with any insecticidal gene but is described here using as an example a peroxidase coding sequence. One to four 4 cm sections are cut from an extended leaf of a transformed maize plant. Each leaf piece is placed on a moistened filter disc in a 50×9 mm petri dish. Five neonate larvae of the target insect (European corn borer, fall armyworm, corn earworm, beet armyworm and black cutworm) were placed on each leaf piece. Since each plant was sampled multiple times this makes a total of 5–20 larvae per plant. The petri dishes were incubated at 30° C. and leaf feeding damage and mortality data were scored at 24, 48, and 72 hours. The toxicity data is shown in Table I.

TABLE I. Mortality values of different insects when exposed to corn leaves expressing the peroxidase enzyme.

|  | 554–1 | 554–3 |
|---|---|---|
| Ostrinia nubilalis (ECB) | 100% | 100% |
| Spodoptera frugiperda (FAW) | 15% | 15%* |
| Spodoptera exigua (BAW) | 0% | 5% |
| Heliothis zea (CEW) | 100% | 100% |
| Agrotis ipsilon (BCW) | 0% | 0% |

*These leaves had a strong antifeeding effect against fall armyworm.

Transgenic Decendants

Transgenic maize plants from event numbers 554 and 755 (which have shown to possess insecticidal properties against European corn borer under in vitro bioassays) were subjected to field trials. When plants in the field reached about 40 cm of extended leaf height, infestations with ECB larvae was begun. About 300 neonate larvae mixed with corn cob grits were deposited into the whorl of each plant. Infestations continued on a weekly basis for four weeks to simulate first generation corn borer (ECB1). Starting two weeks after the initial infestation, each plant was rated weekly, and a mean ECB1 damage rating was scored (see Tables II and III). As corn plants reached anthesis, 300 neonate larvae/plant were applied weekly for four weeks to simulate second generation infestation (ECB2). About 50 days after the initial ECB2 simulated infestation, stalks were split, the tunnel damage measured (see Tables II and III). The experimental conditions are further detailed by Koziel et al. Bio/Technology 11:194–200 (1993).

TABLE II

| Plant Crosses Plant Number | ECB1 foliar damage rating[1] | ECB2 Tunnel length[2] (cm) |
|---|---|---|
| (CG00526 × 554–3) 5 self | | |
| Plant #10 | 1 | 58 |
| Plant #15 | 1 | 15 |
| Plant #22 | 1 | 8 |
| (CG00526 × 554–3) 6 self | | |
| Plant #4 | 1 | 0 |
| Plant #5 | 2 | 5 |
| Plant #9 | 1 | 7 |
| Plant #14 | 2 | 5 |
| Plant #19 | 1 | 4 |
| Plant #20 | 1 | 3 |
| Plant #25 | 1 | 0 |
| Plant #28 | 1 | 9 |
| Plant #29 | 1 | 7 |
| Plant #32 | 1 | 0 |
| Number of positives evaluated | | 13 |
| Total tunneling | | 121 |
| Mean | | 9.3 |
| Standard Deviation | | 15 |
| Non-transformed CG00526) | | |
| 1 | | Dead Plant, Killed by ECB |
| 2 | | Dead PIant, Killed by ECB |
| 3 | | Dead Plant, Killed by ECB |
| No. of negatives evaluated | | 3 |
| Total tunneling | | |
| Mean | | |
| Standard Deviation | | — |

[1]Foliar Damage ratings were determined as follows:
1. No visible leaf injury.
2. Evidence of fine "window pane" damage only on the unfurled leaf where larvae plus corn cob grits fell into the whorl. No pin hole penetration of leaf.
3. Evidence of fine "window pane" damage on two unfurled leaves where larvae plus corn cob grits fell into the whorl. No pin hole penetration of leaf.

TABLE II-continued

| Plant Crosses Plant Number | ECB1 foliar damage rating[1] | ECB2 Tunnel length[2] (cm) |
|---|---|---|

4. Evidence of pin hole or shot hole feeding damage that penetrated the leaf on two or more leaves that emerged from the whorl. (any lesion <0.25" in length).
5. Elongated lesions and/or mid rib feeding evident on more than 3 leaves that emerged from the whorl. Lesions <1.0" in length.
6. Several leaves with elongated lesions (0.75" to 1.5" in length) and/or no more than one leaf with broken mid rib.
7. Long lesions (>1.0") common on about one-half of leaves and/or 2 or 3 leaves with broken mid ribs.
8. Long lesions (>1.0") common on about two thirds of leaves and/or more than 3 leaves with broken mid ribs.
9. Most leaves with long lesions. Several leaves with broken mid ribs. Possibly stunted plants due to ECB feeding.

[2] The extent of internal ECB tunneling damage in a 92 cm section of stalk, 46 cm above and below the primary ear node was measured on transgenic and control plants. The maximum damage that can be rated is 92 cm. Control plants were completely destroyed by the end of the experiment therefore no measurement was possible.

TABLE III

| Plant Crosses Plant Number | ECB1 foliar damage rating[1] | ECB2 damage Tunnel length[2] (cm) |
|---|---|---|
| (CG00714 × 755–9) Positive Segregants | | |
| Plant #6 | 3 | 15 |
| Plant #12 | 3 | 31 |
| Plant #16 | 3 | 19 |
| Plant #20 | 4 | 24 |
| Plant #24 | 3 | 18 |
| PIant #25 | 1 | 26 |
| (CG00714 × 755–9) Negative Segregants | | |
| Plant #7 | 7 | dead plant |
| Plant #8 | dead plant | dead plant |
| Plant #9 | 7 | dead plant |
| Plant #10 | 7 | dead plant |
| Plant #11 | 9 | dead plant |
| Number of positives evaluated | | 6 |
| Total tunneling | | 133 |
| Mean | | 22.17 |
| Standard Deviation | | 5.91 |
| No. of negatives evaluated | | 5 |
| Total tunneling | | |
| Mean | | |
| Standard Deviation | | — |

[1]Foliar Damage ratings were determined as follows:
1. No visible leaf injury.
2. Evidence of fine "window pane" damage only on the unfurled leaf where larvae plus corn cob grits fell into the whorl. No pin hole penetration of leaf.
3. Evidence of fine "window pane" damage on two unfurled leaves where larvae plus corn cob grits fell into the whorl. No pin hole penetration of leaf.
4. Evidence of pin hole or shot hole feeding damage that penetrated the leaf on two or more leaves that emerged from the whorl. (any lesion <0.25" in length).
5. Elongated lesions and/or mid rib feeding evident on more than 3 leaves that emerged from the whorl. Lesions <1.0" in length.
6. Several leaves with elongated lesions (0.75" to 1.5" in length) and/or no more than one leaf with broken mid rib.
7. Long lesions (>1.0") common on about one-half of leaves and/or 2 or 3 leaves with broken mid ribs.
8. Long lesions (>1.0") common on about two thirds of leaves and/or more than 3 leaves with broken mid ribs.
9. Most leaves with long lesions. Several leaves with broken mid ribs. Possibly stunted plants due to ECB feeding.
[2]The extent of internal ECB tunneling damage in a 92 cm section of stalk, 46 cm above and below the primary ear node was measured on transgenic and control plants. The maximum damage that can be rated is 92 cm. Control plants were completely destroyed by the end of the experiment therefore no measurement was possible.

EXAMPLE 2

Transgenic Wheat Plants Comprising a Peroxidase Coding Sequence pJS20293 (FIG. 1) and pUBIAc (FIG. 2) are used to transform wheat using the methods of Chang et al., WO 94/13822, Weeks et al., *Plant Physiol.* 102:1077–1084 (1993) or Nehra et al., *The Plant Journal* 5(2):285–297 (1994).

Transformation of wheat using one method of Chang et al., WO 94/13822 is briefly set forth as follows (others methods set forth in Chang et al. can also be used):

Preparation of Wheat Callus, Genotype UC703

Wheat plants of genotype UC703 are grown to flowering and self-pollinated. Spikes containing embryos 1 to 2.5 mm in length are removed from the plants and sterilized with 10% Clorox solution for 10 minutes. Embryos are removed from the immature seeds and placed with the embryo axis downwards on the medium on Murashige and Skoog containing 5 or 10 mg/l 2,4-D, 13.7% w/v maltose, 100 mg/l proline and 100 mg/l myo-inositol solidified with 0.7–0.8% v/v phytagar or 0.1–0.2% gelrite (initiation medium). After a three week culture in the dark at 27° C, a preferred callus is recognized by the presence of well formed globular, somatic embryos (Type M callus) developing on the scutellum of certain explants. These calli are removed and placed either on MS medium containing 1.0 to 5.0 mg/l 2,4-D and 2–3% sucrose or on a medium containing a reduced level (5%) of maltose before being placed on the sucrose medium. The material is then subcultured every week to fresh MS medium containing 3% sucrose.

Cell Preparation for Bombardment

The cells for bombardment are given a plasmolysis treatment before and after bombardment. Packed cell volume is measured and cells are diluted in 1 MS liquid medium with added osmoticum: 0.4 M sorbitol for suspension cells and 0.6 M sorbitol for callus cells. Cells are diluted such that the final packed cell volume per target is $\frac{1}{30}$ ml for a fine suspension and $\frac{1}{10}$ ml for callus. Diluted cells are placed in a 250 ml flask containing a stir bar and stirred for a minimum of 30 minutes, up to few hours. To plate the cells, 2 ml are withdrawn from the flask and pipetted into the top of a vacuum flask onto which a Whatman 2.5 cm GFA filter is placed. The vacuum is applied until the cells are dried onto the filter. The filters are placed on 60×15 mm petri plates containing 5 ml of solid post-bombardment plasmolysis medium, which is 1 MS containing 0.2 M sorbitol for suspension cells or 0.4 M sorbitol for callus cells. Two filters are plated on each dish.

Vectors Used for Bombardment

The following vectors into which an expression cassette containing peroxidase is inserted can used for particle bombardment (in addition to the cotransformation of pJS20293 (FIG. 1) and pUBIAc (FIG. 2) using equal amounts of DNA):

pSOG30 is a β-glucuronidase (Gus) expression vector derived from plasmid pBI121, purchased from Clontech Laboratories, Palo Alto, Calif. Intron 6 of the maize Adh 1 gene is amplified by PCR from plasmid pB428, described in Bennetzen et al., *Proc. Natl. Acad. Sci. USA* 81:4125–4128 (1987) and ligated into the BamHI site of pBI121, which is between CaMV 35S promoter and the Gus gene. A 17 bp maize chlorotic mottle virus (MCMV) leader, described in Lommel et al., *Virology* 181:382–385 (1991), is inserted into the 35S-Gus gene non-translated leader. The final gene fusion contains the structure: 35S promoter-Adh1 intron 6-MCMV leader-Gus-Nos terminator, all in the pUC19 vector backbone.

pSOG35 is a dihydrofolate reductase (dhrf) expression vector. This construct is derived by fusing the 35S promoter, Adh 1 intron 6, and MCMV leader described above to the dhfr gene from plasmid pHCO, described in Bourouis and Jarry, *EMBO J* 2:1099–1104 (1983). The final gene fusion contains the structure: 35S promoter-Adh 1 intron 6-MCMV leader-dhfr-Nos terminator, all in the pUC 19 vector backbone.

pTG48 comprises the Gus gene under control of the anther specific ant43D promoter and a dhfr gene in a pUC19 backbone. It is the result from the combination of 4 different DNA fragments. Fragment 1 is obtained from pSOG35 after restriction cutting with HindIII and EcoRI. The EcoRI end of the isolated fragment containing the dhfr gene is adapted to a SalI restriction end. Fragment 2 consisted of the anther specific ant43D promoter isolated from plasmid pCIB 3178 after restriction cutting with HindIII and XbaI. Plasmid pCIB 3178 is described in detail in the European patent application number 93810455.1, the relevant parts of which are incorporated herein by reference and was deposited under accession no. NRRL B-18978. Fragment 3 is obtained from plasmid pSOG30 after restriction cutting with XbaI and EcoRI and contained the Gus gene, and fragment 4 corresponded to the commercially available vector pUC19 cut with SalI and EcoRI.

Particle Preparation

Gold particles (1.0 micron; from Bio-Rad) are washed by aliquoting into a microfuge tube, adding ~1 ml 100% ethanol, vortexing, spinning down, removing the supernatant, and repeating twice the sterile water. After the final wash, as much water is removed as possible and polylysine solution (0.02% polylysine+15 mM ammonium acetate) is added to completely immerse the particles. The particles are vortexed, spun, and the supernatant removed. The particles are allowed to dry overnight in a laminar flow hood or for 30 minutes under a gentle nitrogen stream. For a "full" particle preparation 10 mg particles are weighed out and placed in a sterile microfuge tube containing a stir bar. 100 µl (1 µg/µl) of each DNA (alternatively, 50 µl (1 µg/µl) of each DNA) is added, followed by vortexing. Then, 10 µl 100 mM $Na_2HPO_4$ is added, followed by vortexing. 10 µl 100 nM $CaCl_2$ is added, followed by vortexing. Finally, 380 µl 100% ethanol is added, followed by vortexing. While the suspension is stirred vigorously, 3 µl are pipetted onto plastic fliers (projectiles). The particles are allowed to dry onto fliers for at least 15 minutes before bombarding.

Bombarding Cell Cultures

The petri plate containing the cell filters is inverted onto the platform on top of the stage, and centered over the particle flight opening. The clear lid is placed over the top of the platform. A microprojectile is placed onto the breech pin and the breech closed. The "arm" button is pushed to fill the reservoir with the appropriate amount of helium gas (usually 1800–1900 psi). The vacuum on the chamber is pulled to ~27 mm. After the vacuum is turned off, the "arm" and "fire" buttons are pushed. The "arm" button is then pushed to the "off" position. Each filter is usually shot twice.

Post-Bombardment Culture and Selection

After bombardment the cells are kept in the dark overnight. The next day, filters are removed form plasmolysis medium and placed on 1 MS medium. Selection is applied 1–10 days post-bombardment for suspension cells and after 14 days for callus cells. Cells are scraped off the filters and spread onto the surface of plates containing 1 MS plus 2 mg/liter methotrexate (or appropriate selective agent). Plates are incubated in the dark for several weeks. Resistant colonies that arise after a few weeks are transferred to 1

MS+4 mg/l methotrexate (or appropriate selective agent). Colonies that continue to proliferate for about 3–4 weeks are then transferred to "0.5 MS" maintenance medium, which is an aqueous solution of MS salts, vitamins, iron, 3% sucrose, 0.7% agar, 0.5 mg/liter 2,4-D. Tissue is subcultured onto this medium biweekly until embryogenic structures appeared or tissue seemed suitable for regeneration.

Regeneration

Tissue is transferred to MS medium containing either 3 mg/liter BAP or 1 mg/liter NAA+5 mg/liter GA, and plates are moved to the light. After 2–4 weeks, tissue is transferred to MS medium without hormones. Shoots that appeared are placed in containers with either MS medium without hormones or MS medium with 0.5 mg/liter NAA. When sufficient root and shoot growth occurs, plantlets are transferred to soil and placed in a phytotron.

Weeks et al., Plant Physiol. 102:1077–1084 (1993)

Transformation of wheat using the method of Weeks et al., Plant Physiol. 102:1077–1084 (1993) is briefly set forth as follows: wheat plants (*Triticum aestivum* L.) are grown and immature embryos 0.5 to 1 mm in length are excised from greenhouse grown plants (10–18 d after anthesis, depending on the time of year) and placed, scutellum side exposed, on callus maintenance media containing 1.5 mg/L of 2,4-D. Five days after initiation into tissue culture, proliferating callus tissue is visible at the edges of the embryos. At this stage, the embryos are bombarded with gold particles coated with 7 μg of pJS20293 and 7 μg of pUBIAc.

Particle Bombardment

Prior to bombardment, 1 μm gold particles are coated with pJS20293 and pUBIAc DNA by the procedure of Daines, *Biolistic Systems Newsletter* 1:1–4 (1990). A stock suspension of gold particles (Bio-Rad) are suspended at 60 mg/ml in absolute ethanol. Thirty-five microliters of the suspension are aliquoted into 1.5 ml microcentrifuge tubes, washed in sterile distilled water, and resuspended in 25 μl of Tris-EDTA containing 25 μg of supercoiled plasmid DNA. The following solutions are added in order: 220 μl of sterile water, 250 μl of 2.5 M $CaCl_2$, and 50 μl of 0.1 M spermidine (free base). The microfuge tubes are shaken with a vortex mixer at 4° C. for 10 min and centrifuged at 16,000g for 5 min. The supernatant is removed and the pellet is washed with 600 μl of ethanol. The DNA coated gold pellets are resuspended in 36 μl of ethanol. For bombardment, 10 μl of the DNA-gold suspension is placed in the center of a macroprojectile (aka. carrier sheet).

Approximately 25 embryos are placed in the center of a 15×100 mm Petri dish containing callus maintenance medium solidified with 0.35% Phytagel. After 5 d in culture, the embryo-derived calli are bombarded under vacuum with pJS20293-coated gold particles, using the helium-driven DuPont Biolistic Delivery System and disposable components supplied by Bio-Rad. The distance from the stopping plate to the target is 13 cm, and the rupture disc strength is 1100 p.s.i. Immediately after bombardment, calli are transferred to MS selection media containing the appropriate amount of selective agent as can be determined by one skilled in the art.

Regeneration of Wheat Plants

For regeneration, embryogenic calli are transferred to MS medium containing 0.5 mg/l dicamba as described by Hunsinger and Schauz, *Plant Breeding* 98:119–123 (1987). Calli-derived shoots are transferred to Pyrex culture test tubes containing rooting media composed of half-strength MS without hormones. For selection after bombardment, agar media at each stage is supplemented with the appropriate amount of selective agent as can be determined by one skilled in the art.

Plantlets are transferred from rooting media to pots of soil mixture and acclimated to lower humidity at 21° C. in an environmental chamber. After 2 weeks, plants are transferred to the green house. These primary transgenic regenerants are called $T_o$ plants.

Analysis of Transgenic Plants

Transgenic tissues and plants are analyzed using Southern and northern techniques to demonstrate the presence of the peroxidase coding sequence and RNA, respectively.

Wheat plants demonstrated to contain the peroxidase coding sequence by Southern analysis are evaluated for insecticidal activity against *Pseudaletia unipunctata*, army worm; *Spodoptera frugiperda*, fall armyworm; *Elasmopalpus lignosellus*, lesser cornstalk borer; *Agrotis orthogonia*, pale western cutworm; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; or *Aceria tulipae*, wheat curl mite using techniques well known in the art. Those transgenic wheat plants having insecticidal properties are subjected to field trials.

EXAMPLE 3

Transgenic Sorghum Plants Comprising a Peroxidase Coding Sequence pJS20293 (FIG. 1) and pUBIAc (FIG. 2) are used to transform sorghum using the method of Casas et al, *Proc. Natl. Acad. Sci. USA* 90:11212–11216 (December 1993) as is briefly described as follows.

Microprojectile Bombardment

Experiments are conducted with the Biolistics PDS 1000/He system (Sanford et al., *Technique J. Methods Cell Mol. Biol.* 3:3–16 (1991) using tungsten (M-25, 1.7 μm in diameter, DuPont no. 75056) or gold (1.5–3.0 μm in diameter, Aldrich no 32,658–5) microprojectiles. Gold (3 mg) or tungsten (0.75 mg) particles previously washed in ethanol) in aqueous suspension (50 μl) are coated with 5–10 μg of plasmid DNA, as described by the manufacturer (Bio-Rad). Bombardment pressures and distances from the launching plate are experimentally determined.

Immature zygotic embryos, 10–15 per plastic Petri dish (15×60 mm) are bombarded between 24 and 72 hr after culture onto medium. The embryos are transferred onto filter papers (4.5 cm in diameter) that are premoistened but not saturated with liquid medium. The filter papers function to absorb the water from the surface of the embryos, and the embryos are left for 2–3 hrs on the papers prior to bombardment. Immediately after bombardment, the immature embryos are removed from the papers and transferred to semisolid medium.

Transgenic Plant Regeneration and Evaluation for Insect Resistance

Procedures for selection and maintenance of enbryogenic tissue and shoot and root formation from organized structures is as described (Cai & Butler, *Plant Cell Tissue Organ Cult.*, 20:101–110 (1990). The appropriate selective agent as known by one skilled in the art is used.

Transgenic tissues and plants are analyzed using Southern and northern techniques to demonstrate the presence of the peroxidase coding sequence and RNA, respectively.

PAT activity is evaluated in callus and leaf extracts according to DeBlock et al., EMBO J. 6: 2513–2518 (1987).

Sorghum plants demonstrated to contain the peroxidase coding sequence by Southern analysis are evaluated for insecticidal activity against *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranean* granulate cutworm; *Phyllophaga crinita,* white grub; *Eleodes, Conoderus,* and *Aeolus spp.,* wireworms; *Oulema melanopus,* cereal leaf beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Contarinia sorghicola,* sorghum midge; *Tetranychus cinnabarinus,* carmine spider mite; or *Tetranyches urticae,* twospotted spider mite using techniques well known in the art. Those transgenic sorghum plants having insecticidal properties are subjected to field trials.

EXAMPLE 4

Transgenic Rice Plants Comprising a Peroxidase Coding Sequence pJS20293 (FIG. 1) and pUBIAc (FIG. 2) are used to transform rice using the methods of Shimamoto et al., *Nature* 338: 274–277 (1989) (rice); Christou et al., *Biotechnology* 9: 957–962 (1991) (rice); Datta et al., *Bio/Technology* 8:736–740 (1990)(rice) and/or Hayashimoto et al., *Plant Physiol.* 93:857–863 (1990)(rice).

Transformation of rice using the method of Christou et al., *Biotechnology* 9: 957–962 (1991) is briefly set forth as follows:

DNA Preparation

DNA-coated gold particles are prepared by mixing gold particles (10 mg) with a solution of the DNA (20 $\mu$g) in 100 P$\mu$l of buffer (150 mM sodium chloride, 10 mM Tris-HCl, pH 8.0) and vortexed gently for 5–10 seconds. Spermidine (100 $\mu$l of 0.1 M solution) and 100 $\mu$l of a 25% PEG solution (MW 1300–1600) are added with vortexing, followed by the dropwise addition of 100 $\mu$l calcium chloride (2.5M). The mixture is allowed to stand at room temperature for 10 minutes and then spun in a microfuge. The supernatant is removed and the precipitated gold with the DNA complex resuspended in 10 ml of 100% ethanol. The resulting suspension is then coated onto an 18×18 mm carrier sheet at a rate of 163 $\mu$l per carrier sheet, or a calculated rate of 0.05 mg/cm$^2$.

Isolation of Immature Embryos and Preparation for Particle Bombardment

Twelve to fifteen-day old rice immature embryos are harvested from expanded panicles and sterilized with 2% sodium hypochlorite for five minutes. They are subsequently rinsed repeatedly with sterile distilled water and the glumes are removed under a dissecting microscope. The embryos are then aseptically removed and plated on a water-agar plate with the adaxial side in contact with the medium.

Particle bombardment

The carrier sheet bearing the beads is loaded onto the particle accelerator, which uses the discharge of a high voltage capacitor through a small water droplet as the motive force. A 100 mesh retaining screen is placed between the sheet and the target tissue suspended above the machine. The assembly is then evacuated to 500 mm Hg to reduce aerodynamic drag. Ten to sixteen Kv from a 2 $\mu$F capacitor is discharged through a 10 $\mu$l water droplet inside the expansion chamber. The sheet is thus blown against the retaining screen permitting the gold particles to continue onward to impact the target tissue suspended above the screen. The targeted immature embryos are positioned on a water-agar plate so that, when the plate is inserted over the screen, the scutellar region of the embryos would be in the direct path of the accelerated particles.

Plant regeneration

Following particle bombardment, embryos are plated on MS or CC media supplemented with 2.4 D at 0.5 or 2 mg/l and embryogenic callus and plantlets are recovered as described (Hartke, S. and Lara, H., *Genet. & Breed.* 43:205–214 (1989); Datta, S. K. et al., *Plant Sci.* 67:85–88 (1990)).

Recovery of Transformed Embryogenic Callus and Plants

Transformed callus and plants are recovered under both selective and non-selective conditions. In experiments in which selection is incorporated in the transformation/regeneration protocol, the appropriate amount of selective agent as is known by those skilled in the art is used. Putative transformants thus identified, are subjected to molecular and genetic analysis to confirm stable integration and inheritance of the introduced gene.

Analysis of Transgenic Plants

Transgenic tissues and plants are analyzed using Southern and northern techniques to demonstrate the presence of the peroxidase coding sequence and RNA, respectively.

PAT activity is evaluated in callus and leaf extracts according to DeBlock et al., *EMBO J.* 6: 2513–2518 (1987).

Rice plants demonstrated to contain the peroxidase coding sequence by Southern analysis are evaluated for insecticidal activity against *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus leucopterus,* chinch bug; or *Acrosternum hilare,* green stink bug using methods well known in the art.

EXAMPLE 5

Transgenic Oat Plants Comprising a Peroxidase Coding Sequence pJS20293 (FIG. 1) and pUBIAc (FIG. 2) are used to transform oats using the methods of Somers et al., *Bio/Technology* 10:1589–1594 (December 1992)(oat) and/or Torbert et al., *Plant Cell Reports* 14:635–640 (1995)(oat).

Transformation of oats using the method of Somers et al., *Bio/Technology* 10:1589–1594 (December 1992) is briefly set forth as follows:

Cell Cultures

Immature embryos of oat lines derived from GAF-30/Park are used to initiate callus (Rines, H. W. & Luke, H. H., *Theor. Appl. Genet* 71:16–21 (1985)). Friable, embryogenic callus lines are visually selected (Bregitzer, P., et al., *Crop Sci* 29:798–803 (1989)) and subcultured every 2 weeks onto 0.2% Gelrite-solidified MS2D medium containing MS salts (Murashige, T. & Skoog, F., *Physiol. Plant* 15:473–497 (1962)) with 150 mg/l asparagine, 0.5 mg/l thiamine-HCl, 20 g/l sucrose and 2.0 mg/l 2,4-D, pH 5.8. Suspension cultures are initiated by placing approximately 1 g friable, embryogenic callus in 35 ml of liquid MS2D medium. Suspension cultures are selected for the presence of small aggregates of yellow-colored, cytoplasmically-dense cells and subcultured every week.

Preparation of DNA-Coated Particles

Tungsten particles are coated with pJS20293 (FIG. 1) and pUBIAc (FIG. 2) DNA using procedures similar to that described by Gordon-Kamm, et al., *Plant Cell* 2:603–618 (1990)). Prewashed tungsten particles (1.25 mg) are resuspended in 250 μl sterile water in a 1.5 ml Eppendorf tube. A 25 μl aliquot of 1 μg/μl of each DNA, 250 μl of 2.5 M CaCl$_2$ and 50 μl of 0.1 M spermidine (free base) are added to the Eppendorf tube in that order. The mixture is vortexed using a Vortex Genie 2 (Scientific Industries, Inc.) at top speed for 1 min, placed on ice for 5 to 10 min and centrifuged at 14,000 rpm for 1 min in an 5415 Eppendorf centrifuge. Following centrifugation, 550 μl of supernatant is pipetted out and discarded. The DNA-coated tungsten particles are resuspended by pipeting them up and down several times and 1 μl of the DNA-particle suspension is loaded onto the macrocarrier of the particle delivery system.

Delivery of DNA

Suspension culture cells are rinsed 3× with MS2D medium lacking asparagine prior to bombardment. On 3 to 5 days after subculture, suspension culture cells are collected by vacuum filtration onto a 4.7 cm diameter Millipore AP 10, MF support pad (Millipore Corp.) to form an evenly spread thin layer of approximately 0.5 gm fresh weight tissue culture cells. Pads supporting cells are then transferred to 60×20 mm petri dishes. For bombardment of callus, 2-week old friable, embryogenic callus (0.5 gm) is spread evenly over the Millipore support pads premoistened with 2 ml of MS2D medium minus asparagine in 60×20 mm Petri dishes. Petri plates containing suspension or callus samples are positioned (Gordon-Kamm, et al., *Plant Cell* 2:603–618 (1990)) at a distance of 5 cm from the stopping plate and bombarded with the Biolistic PDS-1000 (gun powder) Particle Delivery System (DuPont Co.).

Selection of Transformants

Following bombardment, cells are washed from each Millipore support pad with 5 ml of liquid MS2D medium lacking asparagine into a 60×20 mm petri disk, which is then sealed with parafilm and incubated at 21 to 23° C. in the dark. After 5 days of incubation in liquid medium, bombarded cells are plated in a thin layer onto 7.0 cm diameter Whatman No. 1 filter paper disks overlying Gelrite-solidified MS2D selection medium lacking asparagine and containing 3 mg/l of phosphinothricin (PPT) (Crescent Chemical Co. Inc.). Cells from one bombardment are typically distributed over two or more filter papers depending on the cell density. Filter papers with overlying cells are transferred to fresh selection medium at 2 to 3 week intervals. PPT-resistant colonies begin to appear 7 to 8 weeks post-bombardment and are subcultured directly onto fresh selection medium without filter paper every 2 to 3 weeks thereafter.

Plant Regeneration

PPT-resistant tissue cultures are placed on N+B oat plant regeneration medium (Bregitzer, P., et al., *Crop Sci* 29:798–803 (1989)) (MS salts (Murashige, T. & Skoog, F., *Physiol. Plant* 15:473–497 (1962)), 2 mg/l napthaleneacetic acid, 0.2 mug benzylaminopurine) containing 3 mg/l PPT. After 2 to 6 weeks, shoots are removed from the callus and transferred to MS medium without hormones but containing 3 mg/l PPT for root formation. Rooted plants are transferred to potting soil mix and grown to maturity in growth chambers.

Analysis of Transgenic Plants

Transgenic tissues and plants are analyzed using Southern and northern techniques to demonstrate the presence of the peroxidase coding sequence and RNA, respectively.

PAT activity is evaluated in callus and leaf extracts according to DeBlock et al., *EMBO J.* 6: 2513–2518 (1987).

Oat plants demonstrated to contain the peroxidase coding sequence by Southern analysis are evaluated for insecticidal activity using methods well known in the art.

EXAMPLE 6

Transgenic Barley Plants Comprising a Peroxidase Coding Sequence pJS20293 (FIG. 1) and pUBIAc (FIG. 2) are used to transform barley using the methods of Wan et al., *Plant Physiol.* 104: 37–48 (1994) and/or Jahne et al., *Theor. Appl. Genet.* 89:525–533 (1994).

Transformation of barley using the method of Wan et al., *Plant Physiol.* 104: 37–48 (1994) is briefly set forth as follows:

Plant Materials

Plants of the barley (Hordeum vulgare L.) spring cultivar Golden Promise are grown in growth chambers under a 16-h light/8-h dark period at 12° C. and 60 to 80% humidity (Hunter, C. P., *Plant Regeneration from Microspores of Barley, Hordeum vulgare,* PhD Thesis, Wye College, University of London, Ashford, Kent (1988)). Light levels at head height are approximately 350 to 400 μE. Seeds of a winter cultivar, Igri, are germinated in soil in the growth chamber under the same conditions. When about 10 cm in height, the seedlings are vernalized for 8 weeks under a 10-h light (10–15 μE)/14-h dark period at 4° C. (Hunter, C. P., *Plant Regeneration from Microspores of Barley, Hordeum vulgare,* PhD Thesis, Wye College, University of London, Ashford, Kent (1988)). After vernalization, they are grown under the same regime as Golden Promise plants. All plants are fertilized with Osmocote (Sierra, 17-6-12 plus minors) at the time of planting and then biweekly with 0.02% Verdi (Peter's, 20-20-20).

Immature Embryos and Callus Derived from Immature Embryos

Spikes of cv Golden Promise with immature embryos about 1.5 to 2.5 mm in size are surface sterilized in 20% (v/v) bleach (5.25% sodium hypochlorite) for 5 min, rinsed briefly three times, and washed for 5 min with sterile water. Immature embryos are dissected from young caryopses and left intact or are bisected longitudinally. For induction of callus for bombardment, embryos (intact or bisected) are placed scutellum-side down on callus induction medium, which is Murashige and Skoog medium (Murashige, T. & Skoog, F., *Physiol Plant* 15:473–497 (1962)) supplemented with 30 g/L maltose, 1.0 mg/L thiamine-HCl, 0.25 g/L myo-inositol, 1.0 g/L casein hydrolysate, 0.69 g/L Pro, and 2.5 mg/L dicamba, solidified by 3.5 g/L gelrite (Scott, Carson, CA) or Phytagel (Sigma). Embryos are incubated at 25° C. in the dark, and embryogenic callus is selected for bombardment after 2 weeks.

Anther Culture and Microspore-Derived Embryos

Spikes, wrapped by the flag leaves, are harvested from cv Igri plants when the microspores are at mid-uninucleate to early binucleate stages and surface sterilized briefly with 70% ethanol. Anthers are dissected from spikelets and 60 anthers are placed in each Petri dish (35×10 mm) with 3 mL of 0.3 M mannitol. The Petri dishes are sealed with Parafilm and incubated at 25° C. in the dark for 3 or 4 d. Anthers are subsequently transferred into Petri dishes with 3 mL of Hunter's liquid FHG medium (a modified Murashige and Skoog medium with lower NH$_4$NO$_3$ and high Gln; Kasha, K., et al., "Haploids in Cereal Improvement: Anther and Microspore Culture," J.P. Gustafson, ed., *Gene Manipulation in Plant Improvement II,* Plenum Press, NY (1990), pp. 213–235). without Ficoll-400 and supplemented with 1 mg/L IAA and 0.2 mg/L kinetin (designated as FHG$^+$) and incubated as described. MDEs are visible after approximately 2 or 3 weeks and are used for bombardment after approximately 4 weeks.

Preparation of Bombardment Plates and Microprojectile Bombardment

One day before bombardment, IEs (1.5–2.5 mm) from young caryopses of cv Golden Promise are cut in half longitudinally and placed in three different orientations (scutellum-side up, scutellum-side down, or cut-surface up) on callus induction medium in the center of Petri dishes (100×15 mm). For bombardment of callus, approximately 0.5 g of embryogenic callus from cultured IEs is cut into small pieces (about 2 mm) and placed in the center of a Petri dish (100×15 mm) containing callus induction medium. MDEs are harvested from anther culture plates using a Pasteur pipet and distributed evenly in petri dishes (100×15 mm) on a piece of 5-cm Whatman No. 3 filter paper supported by two 7-cm filters. Before bombardment, excess medium is removed from the filters.

Plasmid DNA is adsorbed to gold particles (1.0 μm, Dupont, Wilmington, Del.) as described previously (Daines, R. J., *Biolistic Particle Delivery Systems Newsletter* 1:1, 4 (1990)). When two plasmids are used, equal amounts (μg) of DNA from the two plasmids are mixed. All target materials are bombarded once, using DuPont PDS 1000 He Biolistic Delivery System. The target materials are positioned approximately 13 cm below the microprojectile stopping plate; 1100-p.s.i. rupture discs are used.

Selection Transformants

IEs and Callus

One day after bombardment, half-embryos and callus pieces are transferred individually to callus induction medium with 5 mg/L bialaphos; the half-embryos are cultured scutellum-side down, irrespective of their orientation during bombardment. Tissue remains on the first selection plate for approximately 10 to 14 d. At transfer to the second selection plate (5 mg/L bialaphos), individual callusing embryos or callus pieces are broken using forceps into several small pieces and maintained separately. During the subsequent two to three selection passages (each approximately 10 to 20 d, at 5 mg/L bialaphos), callus pieces showing evidence of more vigorous growth are transferred earlier to new selection plates and tissue is handled in an identical manner. All callus tissue which develops originally from each piece of embryo or callus is defined as a line. Bialaphos-resistant callus lines are maintained by monthly subculture on callus induction medium with 5 mg/L bialaphos.

MDEs

Following bombardment, several drops of FHG+ medium are added to the MDEs. After 2 or 3 d, embryos of >1.5 mm are transferred individually onto callus induction medium with 3 or 5 mg/L bialaphos. Smaller embryos remain on the filters and are transferred to selection medium when they are approximately 1.5 mm. Filter papers are washed every 2 or 3 d by repeated addition and removal of liquid FHG+ medium. MDEs remain on the first selection medium for 10 to 20 d. MDEs showing evidence of callus formation are transferred to fresh selection medium with 5 mg/L bialaphos. During transfer, each callusing MDE is broken into a few small pieces. Further selection is as described in the previous section.

Plant Regeneration and Herbicide Application

Plants are regenerated from PAT-positive callus lines by transferring embryogenic callus to FHG medium with 1 mg/L bialaphos at 23° or 25° C. under fluorescent lights (45–55 μE, 16 h/d). In approximately 2 weeks, plantlets are observed. Green plantlets, approximately 2 cm, are transferred into Magenta boxes containing plantlet growth medium (hormone-free callus induction medium) with 1 mg/L bialaphos. Before they grow to the top of the box, plantlets are transferred to 6-inch pots containing Supersoil and placed in the greenhouse (16-h light period, 15°–18° C.). Regenerants grow to maturity and are self-pollinated. Some of the plants are tested for their response to Basta (200 g/L PPT, Hoechst AG, Frankfurt, Germany) by spraying with a 0.5% (v/v) solution plus 0.1% Tween 20. Plants are also regenerated from wild-type callus on the media without bialaphos.

Analysis of Transgenic Plants

Transgenic tissues and plants are analyzed using Southern and northern techniques to demonstrate the presence of the peroxidase coding sequence and RNA, respectively.

Barley plants demonstrated to contain the peroxidase coding sequence by Southern analysis are evaluated for insecticidal activity against *Ostrinia nubilalis,* European corn borer; *Agrotis ipsilon,* black cutworm; *Schizaphis graminum,* greenbug; *Blissus leucopterus leucopterus,* chinch bug; *Acrosternum hilare,* green stink bug; *Euschistus servos,* brown stink bug; *Hylemya platura,* seedcorn maggot; *Mayetiola destructor,* Hessian fly; Thysanoptera, Thrips; or *Petrobia latens,* brown wheat mite using methods well known in the art.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method for controlling an insect selected from the group consisting of European corn borer, corn earworm, and fall armyworm, comprising:

feeding or contacting said insect with transgenic maize cells transformed with recombinant DNA comprising a coding sequence encoding anionic peroxidase, wherein expression of anionic peroxidase confers resistance to said insect in said transgenic maize cells.

2. The method according to claim 1, wherein said method comprises:

transforming a maize plant with a DNA sequence comprising a coding sequence encoding anionic peroxidase.

3. The method of claim 1, wherein said anionic peroxidase is a tobacco anionic peroxidase.

4. The method of claim 2, wherein said plant is transformed using a technique selected from the group consisting of particle bombardment, electroporation, and polyethylene glycol treatment.

5. The method of claim 1 wherein said DNA sequence further comprises a selectable or screenable marker gene.

6. The method of claim 5, wherein said marker gene encodes an enzyme selected from the group consisting of neomycin phosphotransferase, hygromycin phosphotransferase, dihydrofolate reductase, phosphinothricin acetyltransferase, 2,2-dichloroproprionic acid dehalogenase, acetohydroxyacid synthase, 5-enolpyruvylshikimate-phosphate synthase, haloarylnitrilase, acetylcoenzyme A carboxylase, dihydropteroate synthase, chloramphenicol acetyl transferase, and β-glucuronidase.

7. The method of claim 1, wherein said coding sequence is comprised within pJS20293 (NRRL B-21626).

8. The method of claim 1, wherein said maize cells are transformed by particle bombardment of immature zygotic embryos.

9. The method of claim 1, wherein said insect is European corn borer.

10. The method of claim 1, wherein said insect is corn earworm.

11. The method of claim 1, wherein said insect is fall armyworm.

12. A method of protecting a maize plant from an insect selected from the group consisting of European corn borer, corn earworm, and fall armyworm, comprising expressing an anionic peroxidase in said maize plant by transforming said maize plant with a chimeric gene comprising:

(a) a nucleic acid promoter sequence that promotes in a plant the transcription of an associated coding sequence at elevated levels, and (b) a nucleic acid coding sequence that encodes anionic peroxidase operatively linked to said promoter sequence, whereby expression of anionic peroxidase in said maize plant protects said maize plant from said insect.

13. The method of claim 12, wherein said anionic peroxidase is a tobacco anionic peroxidase.

14. The method of claim 13, wherein said coding sequence is comprised within pJS20293 (NRRL B-21626).

15. The method of claim 12, wherein said maize plant is transformed using a technique selected from the group consisting of particle bombardment, electroporation, and polyethylene glycol treatment.

16. The method of claim 15, wherein said maize plant is transformed by particle bombardment of immature zygotic embryos.

17. The method of claim 12, wherein said insect is European corn borer.

18. The method of claim 12, wherein said insect is corn earworm.

19. The method of claim 12, wherein said insect is fall armyworm.

20. The method of claim 12, wherein expression of anionic peroxidase in said maize plant protects said maize plant from said insect by killing said insect.

21. The method of claim 12, wherein expression of anionic peroxidase in said maize plant protects said maize plant from said insect by conferring an antifeeding effect against said insect.

* * * * *